United States Patent
Mirochinik et al.

(10) Patent No.: US 11,020,107 B2
(45) Date of Patent: Jun. 1, 2021

(54) SUTURE CAPTURING DEVICE FOR USE IN ARTHROSCOPIC PROCEDURES

(71) Applicants: T.A.G. Medical Devices—Agriculture Cooperative Ltd., Kibbutz Gaaton (IL); Alex Levin, Kiryat Yam (IL)

(72) Inventors: Aryeh Mirochinik, Akko (IL); Shai Nachmias, Nahariya (IL); Roy Zilberman, Qadarim (IL)

(73) Assignee: T.A.G. Medical Devices—Agriculture Cooperative Ltd., Kibbutz Gaaton (IL)

(*) Notice: Subject to any disclaimer, the term of this patent is extended or adjusted under 35 U.S.C. 154(b) by 386 days.

(21) Appl. No.: 15/557,144

(22) PCT Filed: Mar. 9, 2016

(86) PCT No.: PCT/IL2016/050261
§ 371 (c)(1),
(2) Date: Sep. 11, 2017

(87) PCT Pub. No.: WO2016/142944
PCT Pub. Date: Sep. 15, 2016

(65) Prior Publication Data
US 2018/0242968 A1    Aug. 30, 2018

Related U.S. Application Data

(60) Provisional application No. 62/130,040, filed on Mar. 9, 2015.

(51) Int. Cl.
*A61B 17/06* (2006.01)
*A61B 17/04* (2006.01)
*A61B 17/00* (2006.01)

(52) U.S. Cl.
CPC .... *A61B 17/06004* (2013.01); *A61B 17/0469* (2013.01); *A61B 17/0482* (2013.01);
(Continued)

(58) Field of Classification Search
CPC .......... A61B 17/06004; A61B 17/0482; A61B 17/0483; A61B 17/0469; A61B 17/06109;
(Continued)

(56) References Cited

U.S. PATENT DOCUMENTS 5,312,422 A * 5/1994 Trott ................. A61B 17/0469
604/272
5,447,512 A * 9/1995 Wilson ............... A61B 17/0469
289/17

(Continued)

FOREIGN PATENT DOCUMENTS

| WO | WO 2013/027210 | 2/2013 |
| WO | WO 2014/147619 | 9/2014 |
| WO | WO 2016/142944 | 9/2016 |

OTHER PUBLICATIONS

Supplementary European Search Report and the European Search Opinion dated Nov. 7, 2018 From the European Patent Office Re. Application No. 16761206.8. (11 Pages).

(Continued)

*Primary Examiner* — Melanie R Tyson
*Assistant Examiner* — Chima U Igboko

(57) ABSTRACT

A suture capturing device configured to attain multiple preset orientations, comprising: a handle; a hollow shaft coupled to said handle; a rigid needle element configured with a hook for catching a suture and where the needle element is operatively coupled to the hollow shaft opposite the handle and configured to be slidable in a first direction to assume an open orientation where the hook is exposed relative to the hollow shaft and in a second direction to assume a closed orientation where the hook is not exposed relative to the hollow shaft.

21 Claims, 37 Drawing Sheets

(52) U.S. Cl.
CPC .... *A61B 17/0483* (2013.01); *A61B 17/06109* (2013.01); *A61B 2017/00349* (2013.01); *A61B 2017/06009* (2013.01); *A61B 2017/06042* (2013.01)

(58) Field of Classification Search
CPC . A61B 17/0485; A61B 17/29; A61B 17/2909; A61B 2017/0046; A61B 2017/0472; A61B 2017/06014; A61B 2017/06009; A61B 2017/00349; A61B 2017/06042; A61B 2017/291; A61B 2017/2911; A61B 2017/2912; A61B 2017/2925
See application file for complete search history.

(56) References Cited

U.S. PATENT DOCUMENTS

| | | | |
|---|---|---|---|
| 5,499,991 A | 3/1996 | Garman et al. | |
| 5,611,784 A | 3/1997 | Barresi et al. | |
| 5,643,292 A | 7/1997 | Hart | |
| 5,817,111 A | 10/1998 | Riza | |
| 7,704,262 B2 | 4/2010 | Bellafiore et al. | |
| 2004/0073254 A1 | 4/2004 | Wyman et al. | |
| 2006/0069399 A1* | 3/2006 | Weisel | A61B 17/0483 606/148 |
| 2010/0305583 A1 | 12/2010 | Baird et al. | |
| 2011/0022063 A1* | 1/2011 | McClurg | A61B 17/0482 606/145 |
| 2012/0209063 A1* | 8/2012 | Nishtala | A61B 17/32056 600/106 |
| 2014/0039529 A1* | 2/2014 | Torrie | A61B 17/0482 606/148 |
| 2014/0039530 A1 | 2/2014 | Torrie | |
| 2014/0188138 A1* | 7/2014 | Melsheimer | A61B 17/0485 606/144 |
| 2015/0018854 A1* | 1/2015 | Haines | A61B 17/0485 606/148 |

OTHER PUBLICATIONS

International Preliminary Report on Patentability dated Sep. 21, 2017 From the International Bureau of WIPO Re. Application No. PCT/IL2016/050261. (10 Pages).
International Search Report and the Written Opinion dated Oct. 4, 2016 From the International Searching Authority Re. Application No. PCT/IL2016/050261.
Invitation to Pay Additional Fees dated Jul. 28, 2016 From the International Searching Authority Re. Application No. PCT/IL2016/050261.
DePuy Mitek "Expressew® III, Flexible Suture Passer: Surgical Technique Guide", DePuy Mitek Inc., 8 P., 2011.
Pivot Medical "NanoPass® Suture Managers. Sometimes, Smaller Is Better", Pivot Medical Inc., A Stryker Sports Medicine Company, Datasheet, 2 P., 2016.

* cited by examiner

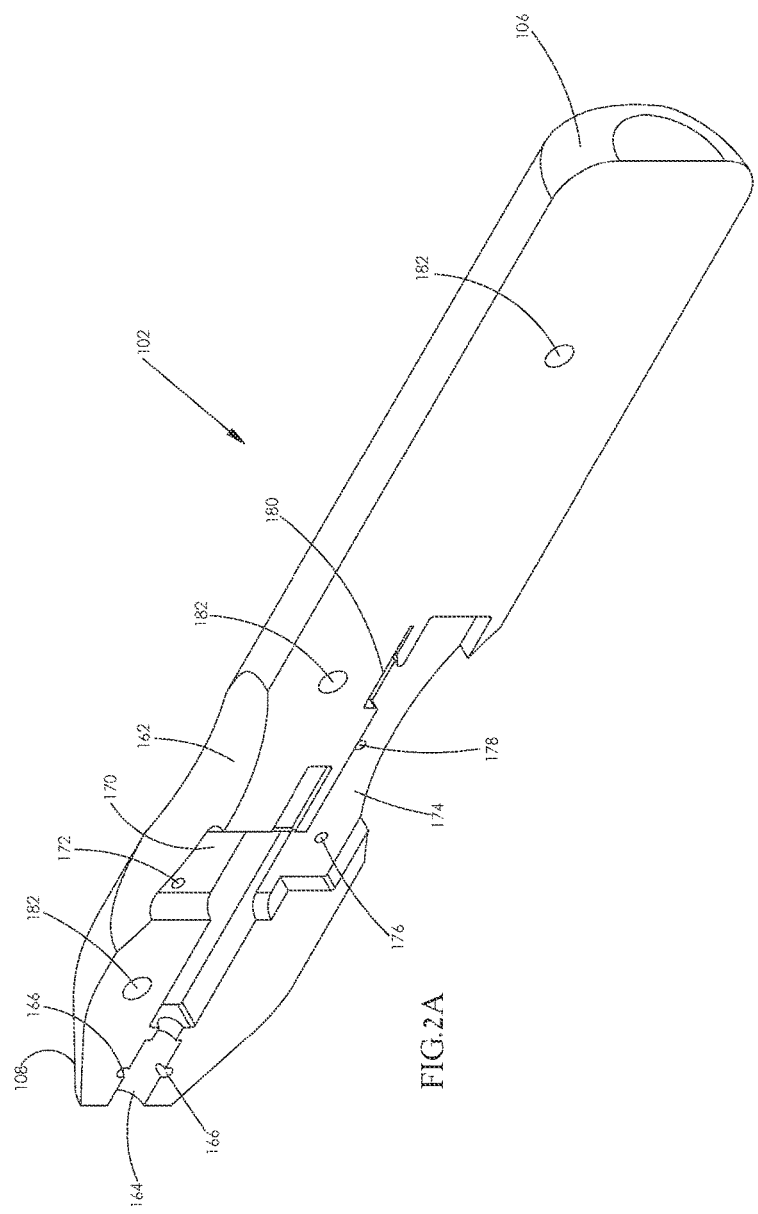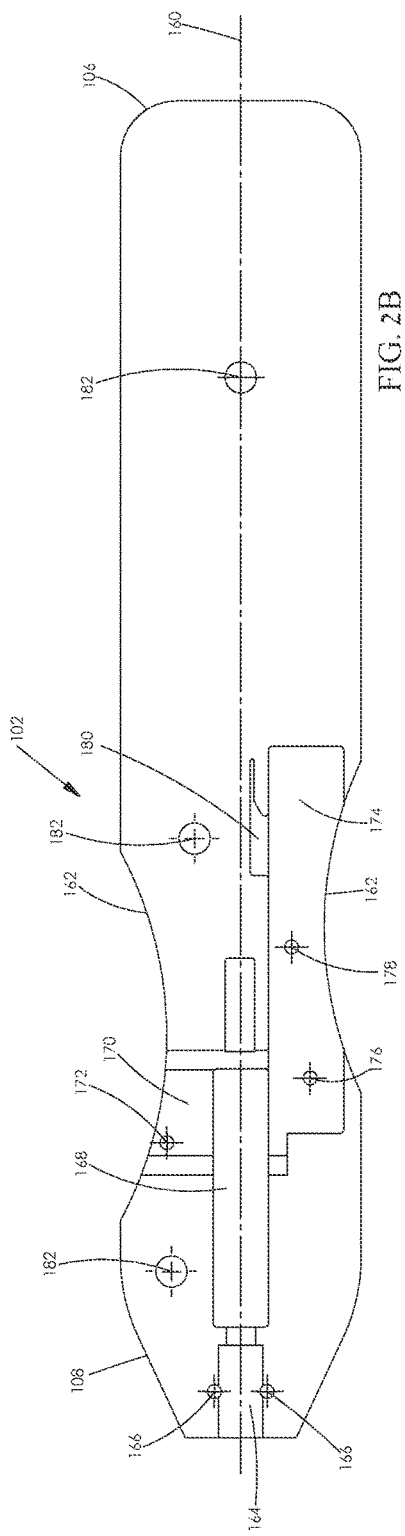

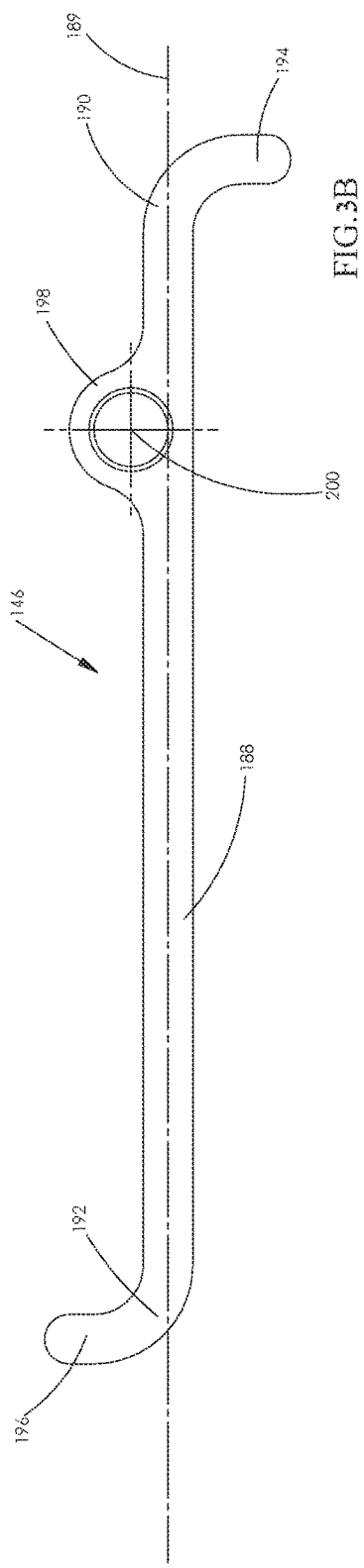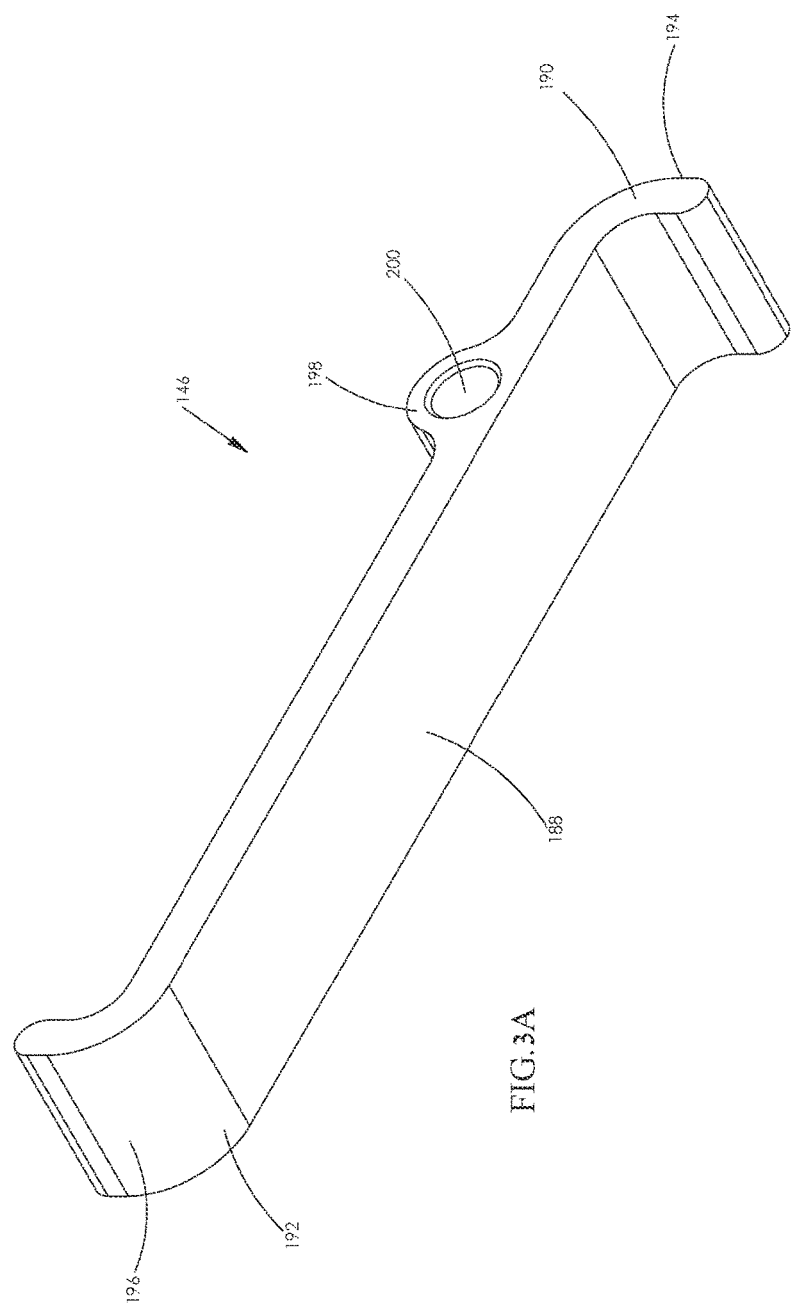
FIG. 3B
FIG. 3A

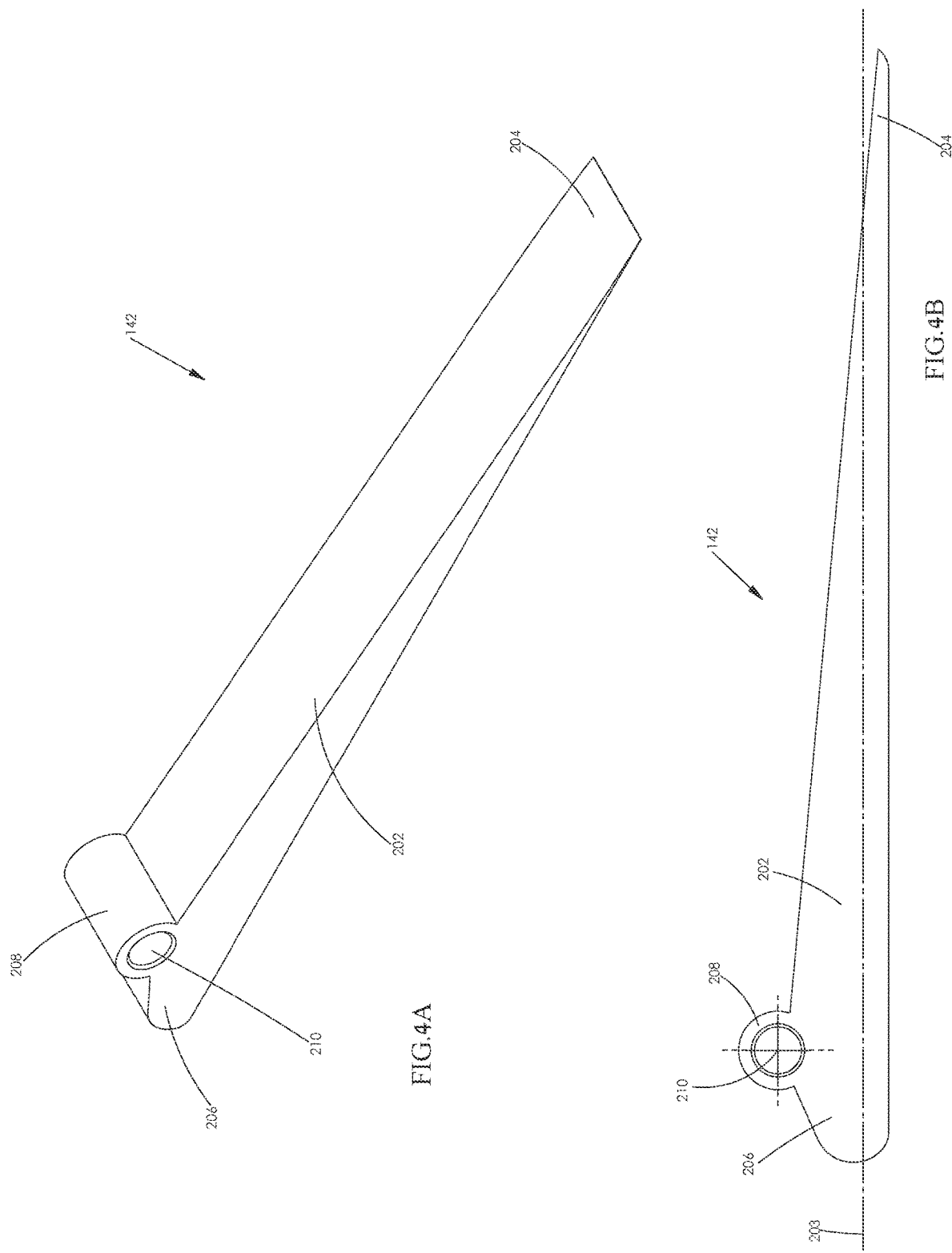

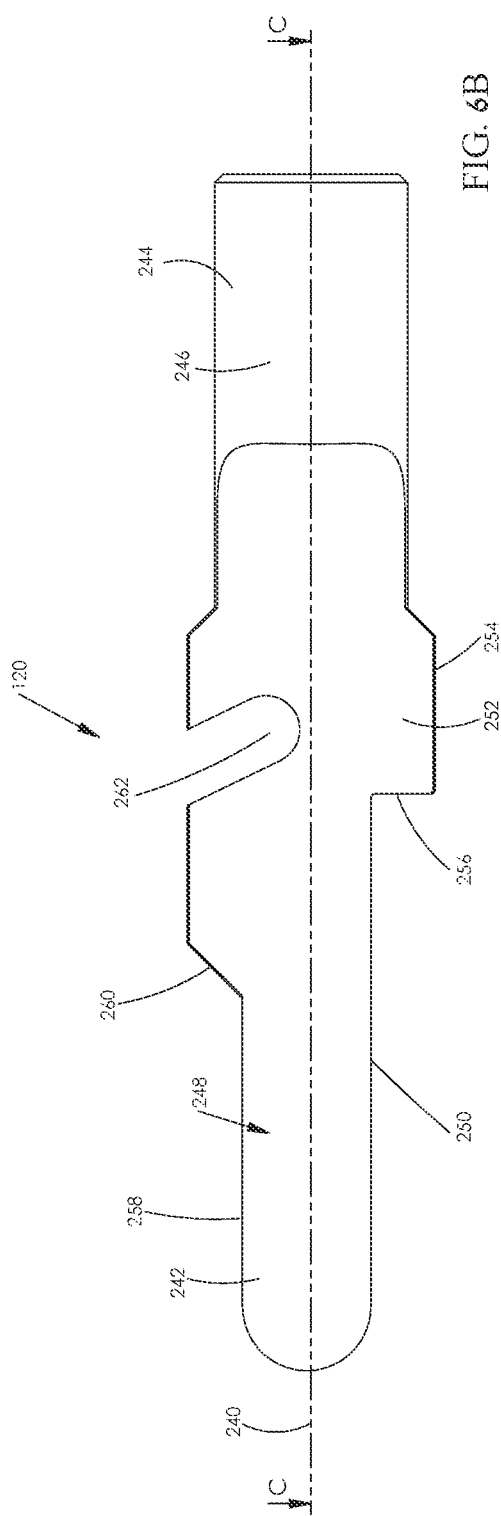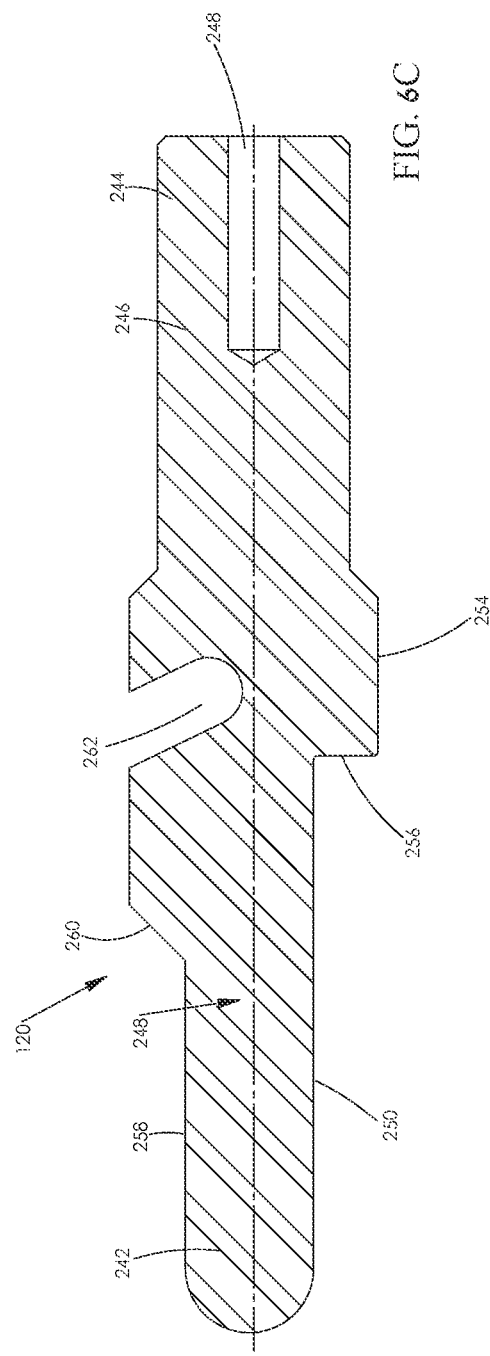

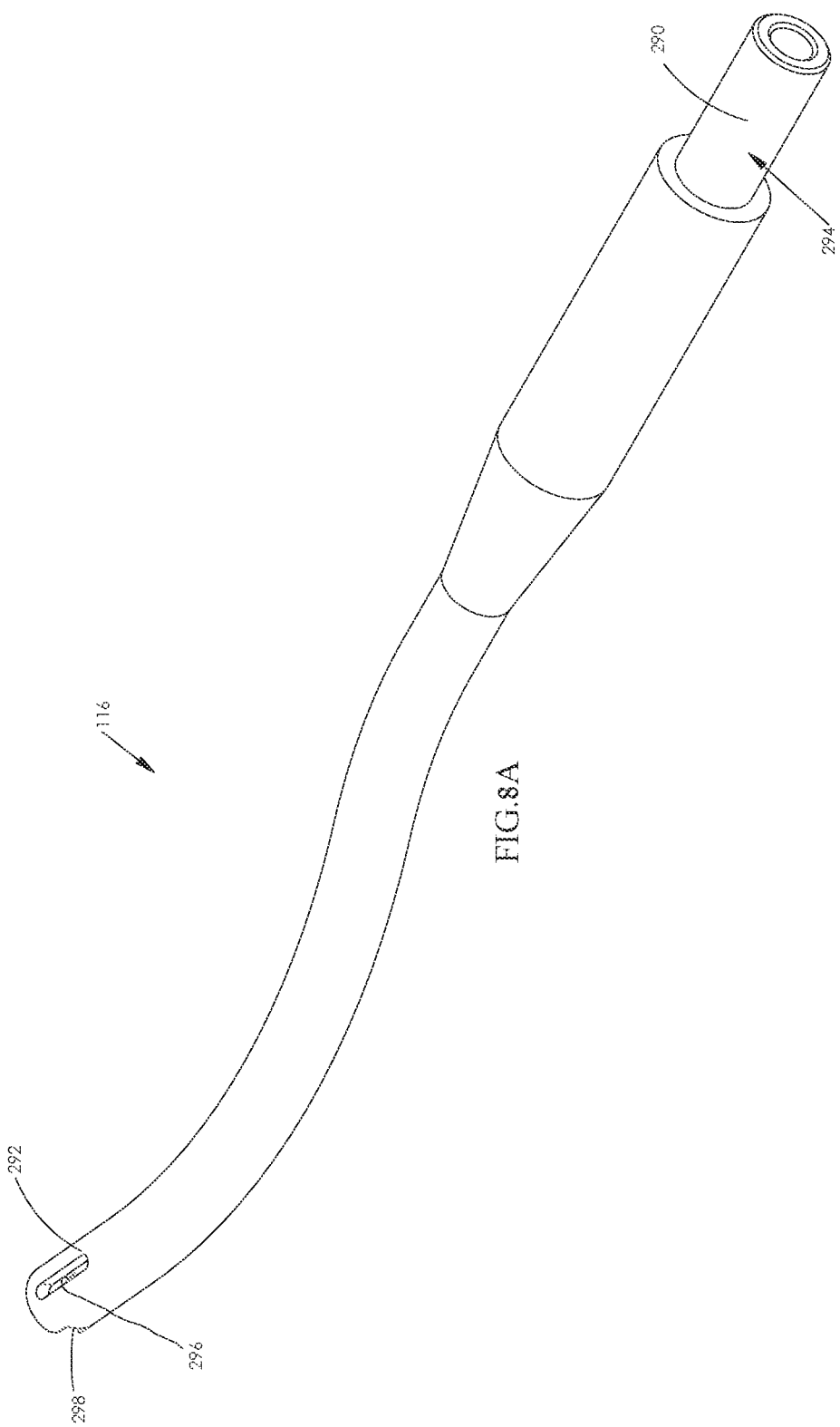

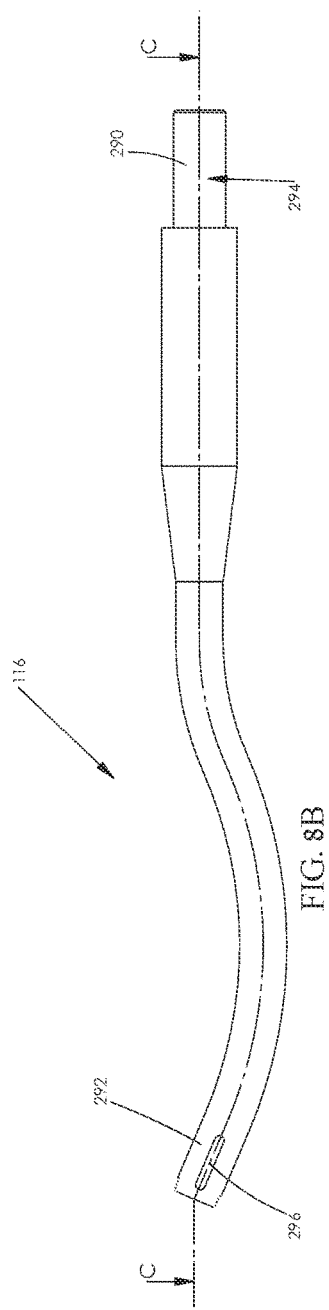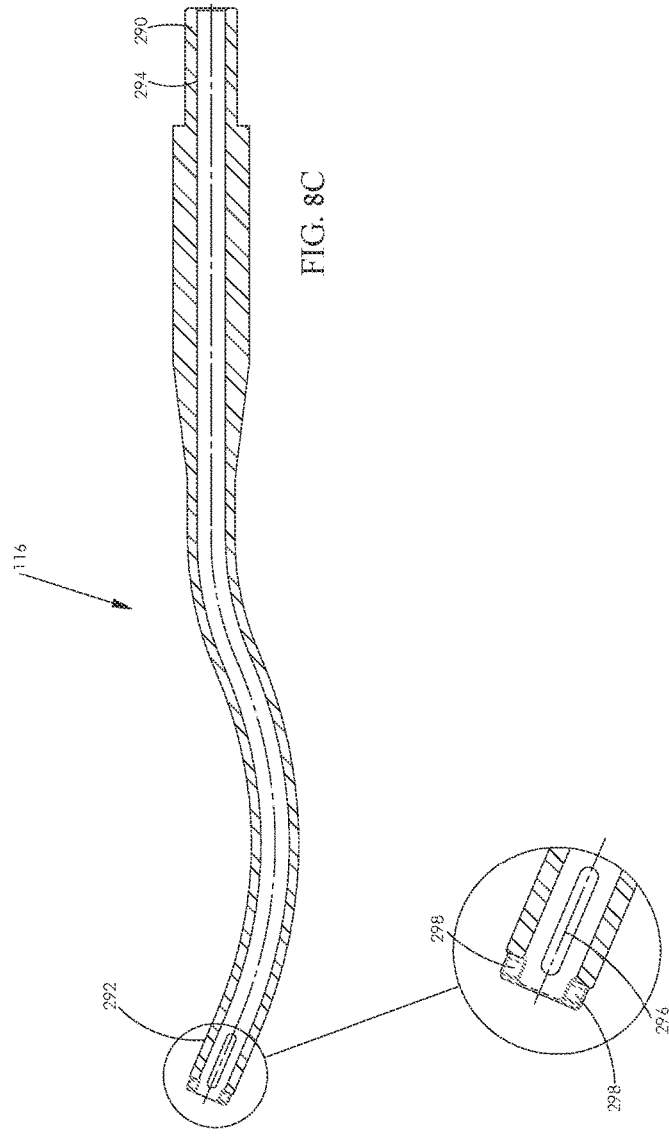

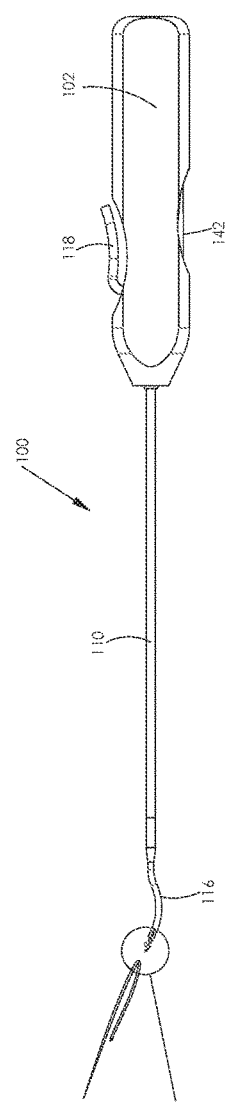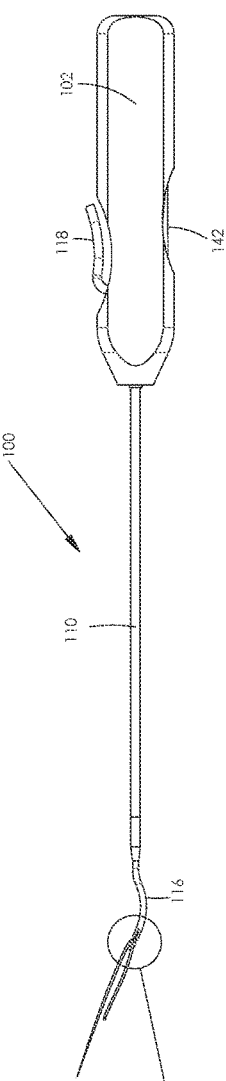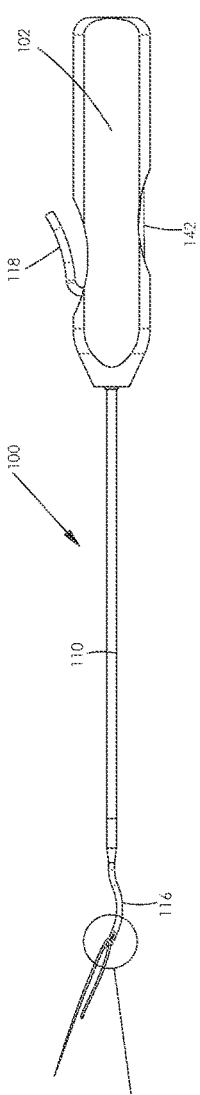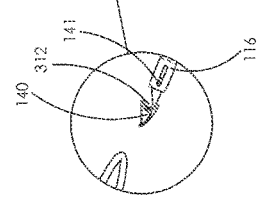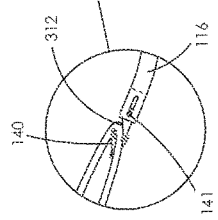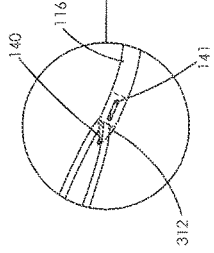
FIG. 13
FIG. 14
FIG. 15
FIG. 16

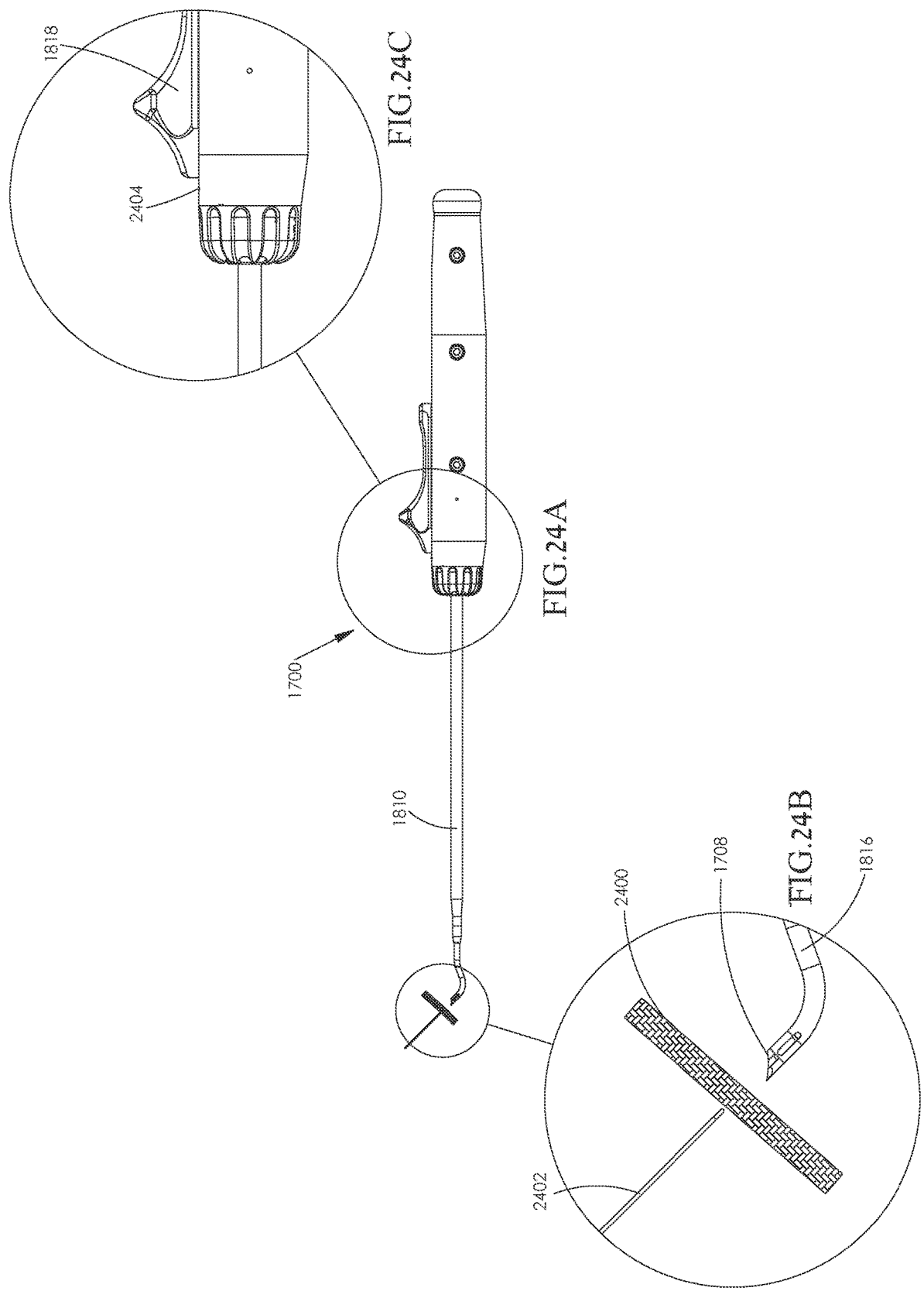

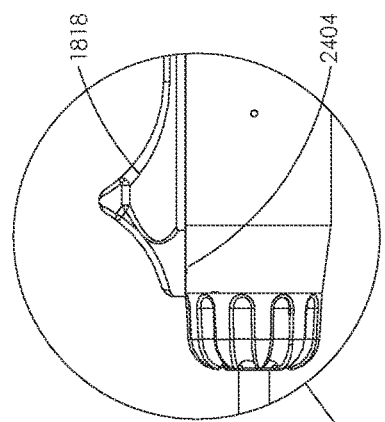
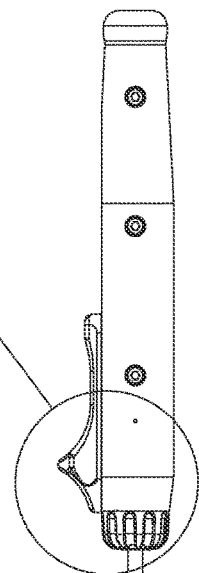
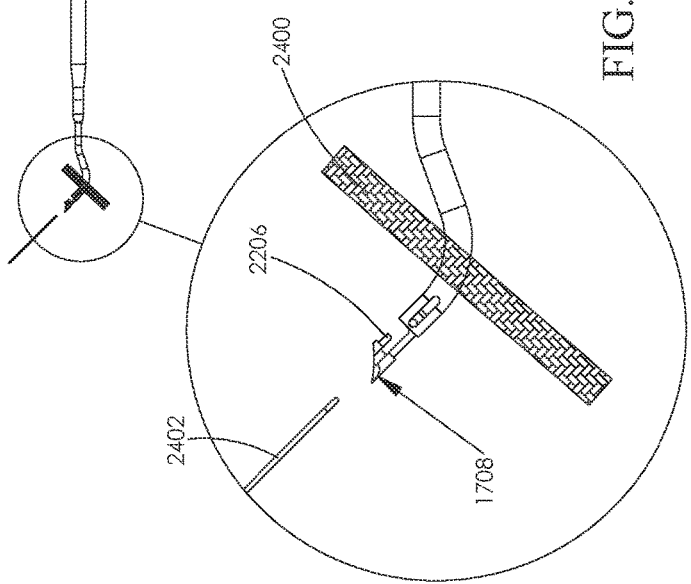
FIG.25C
FIG.25A
FIG.25B

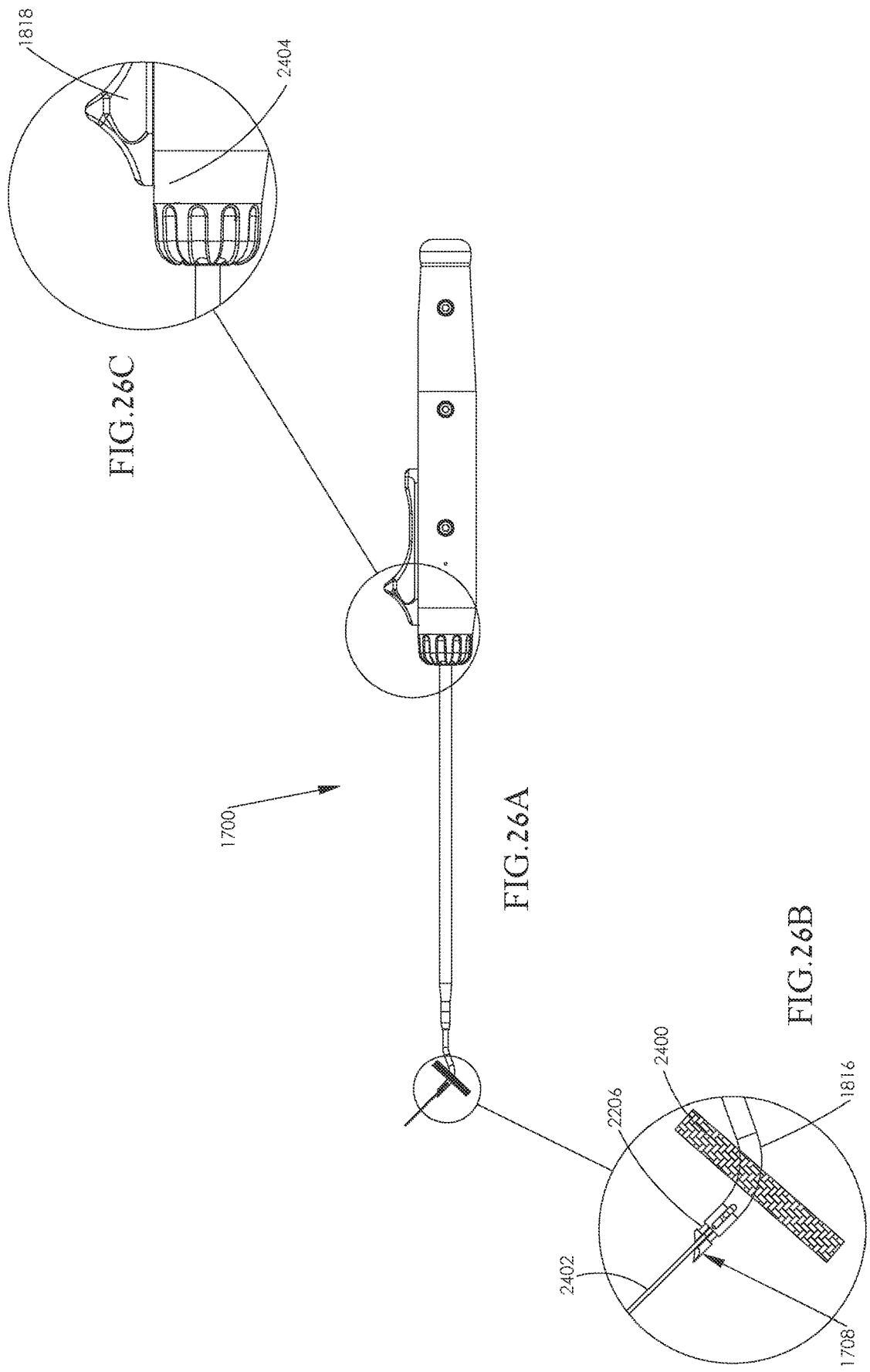

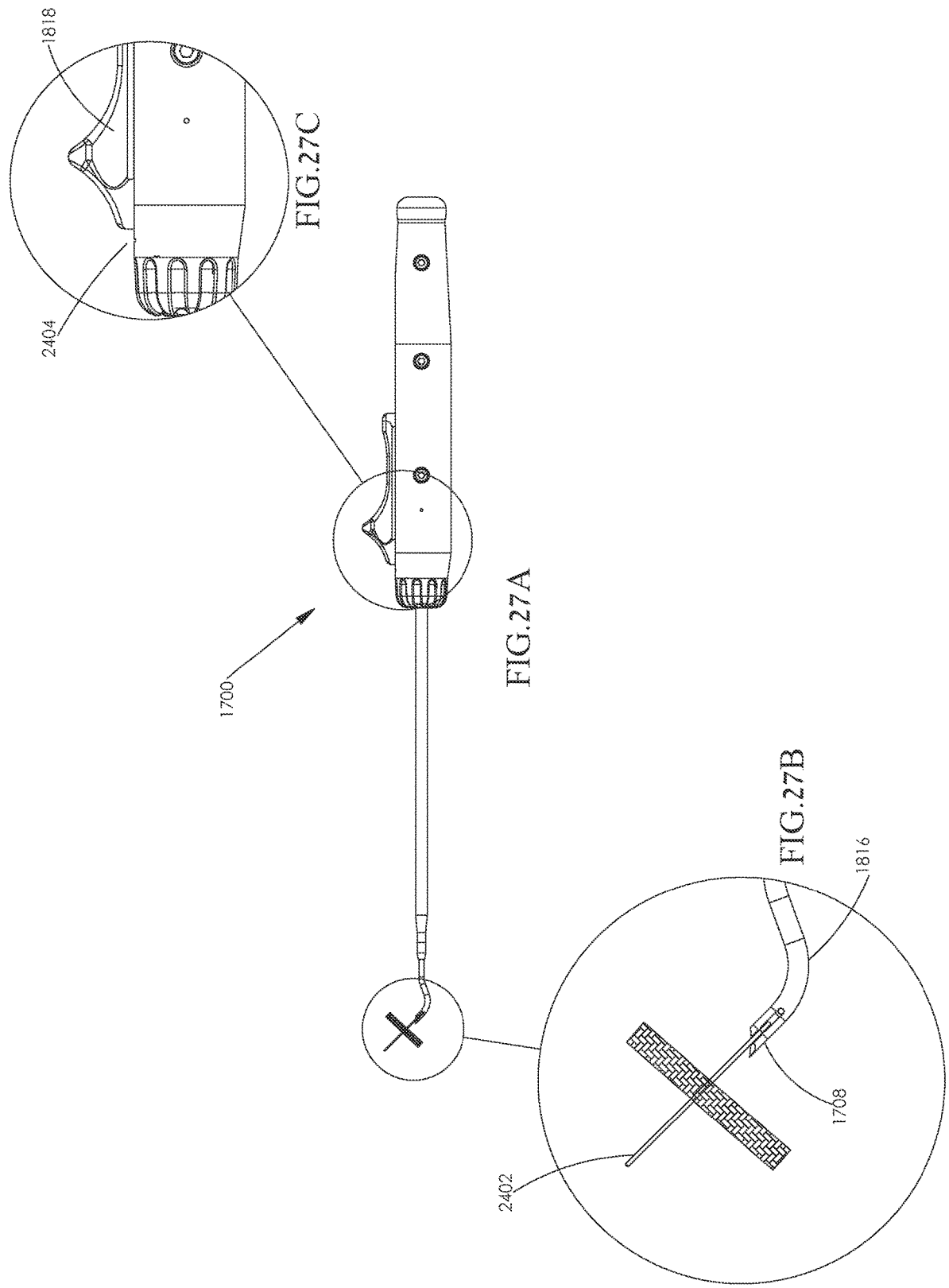

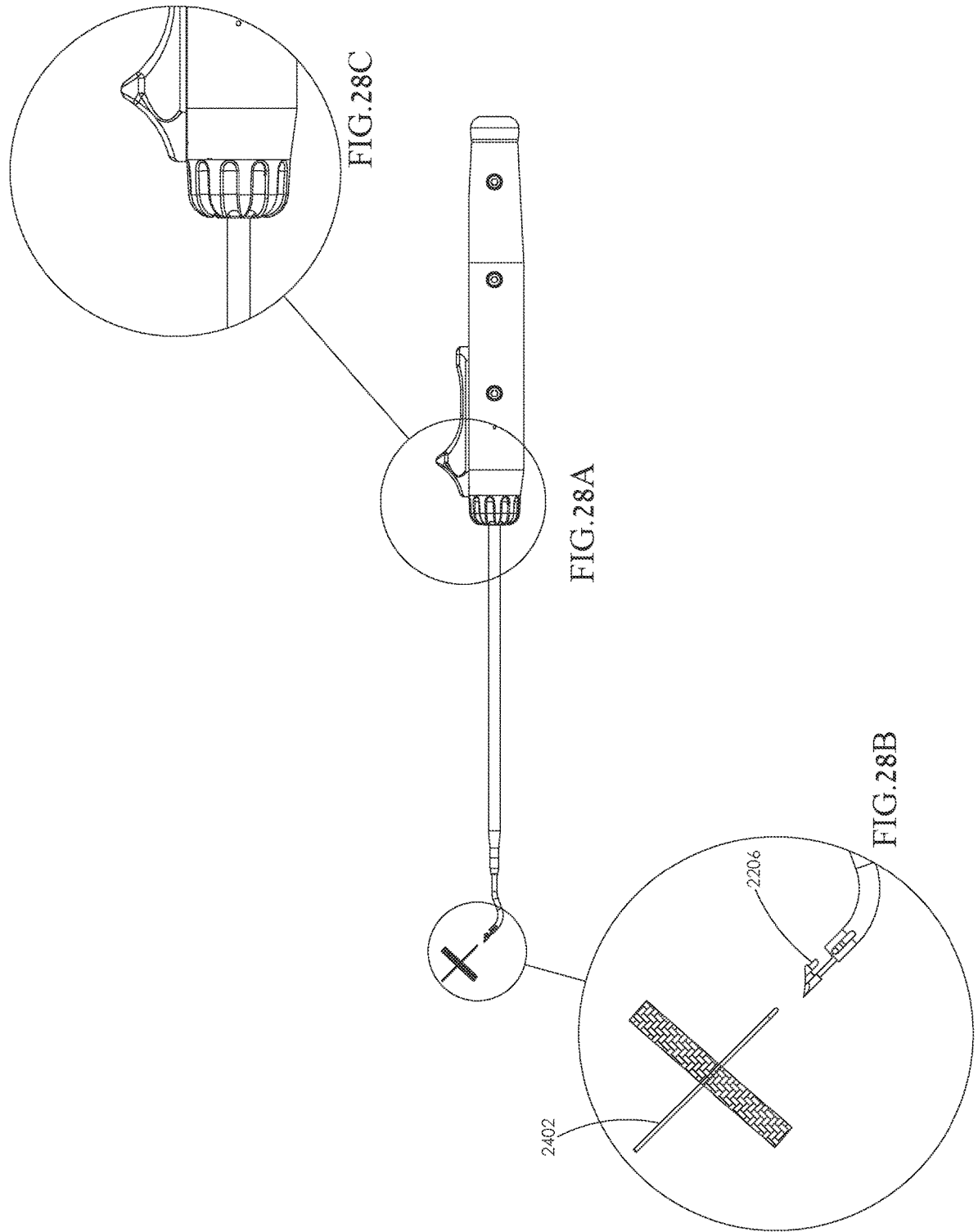

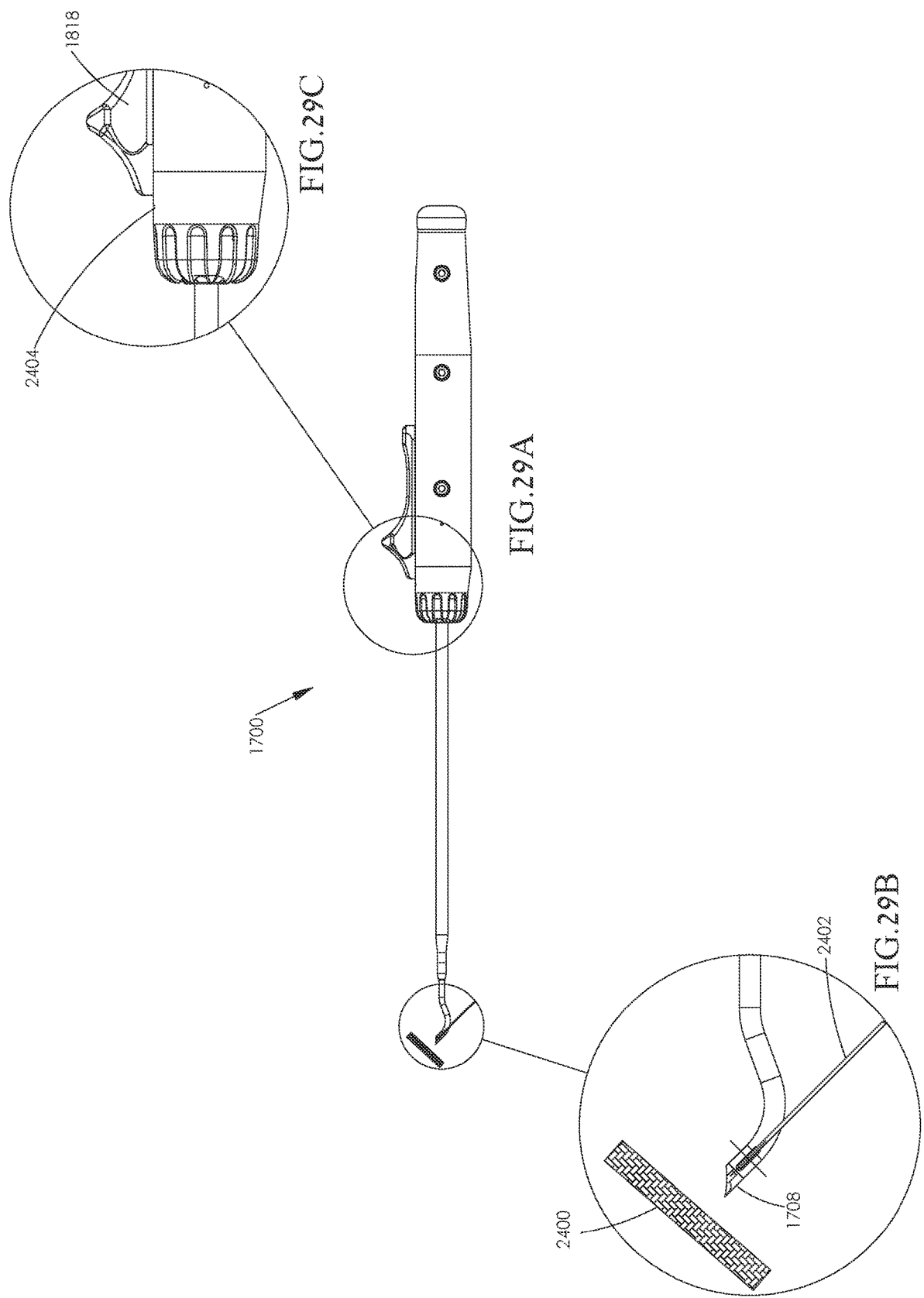

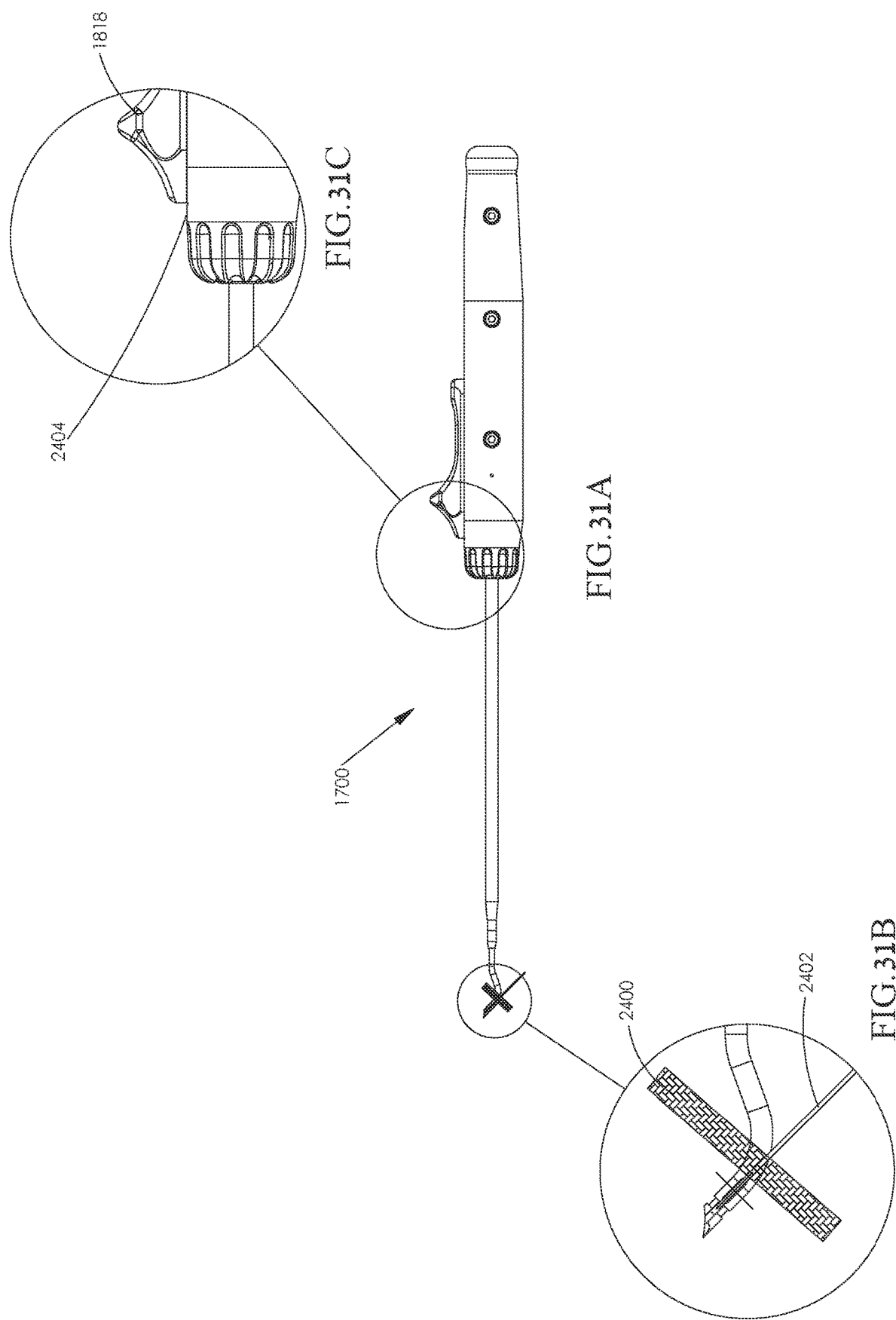

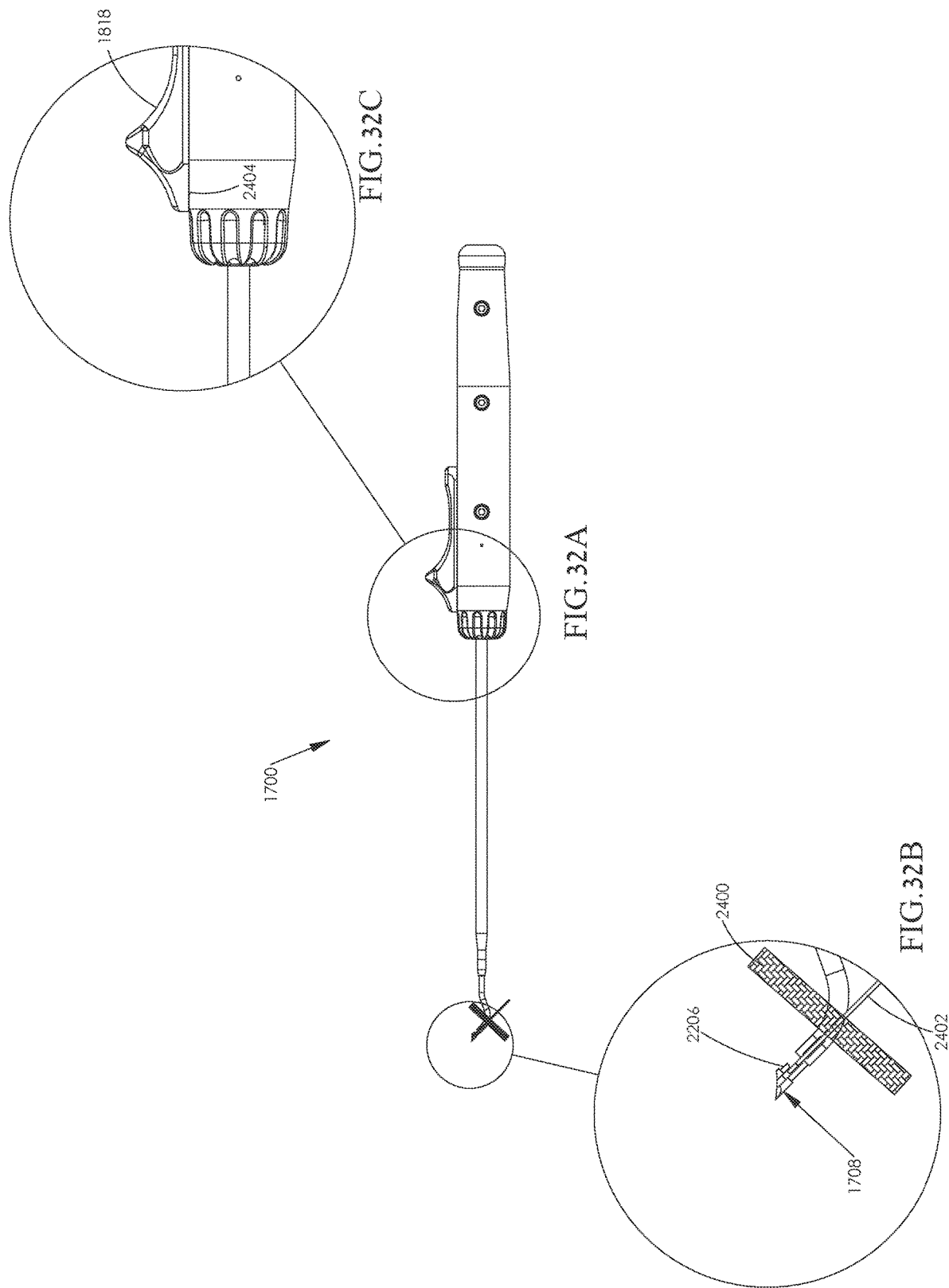

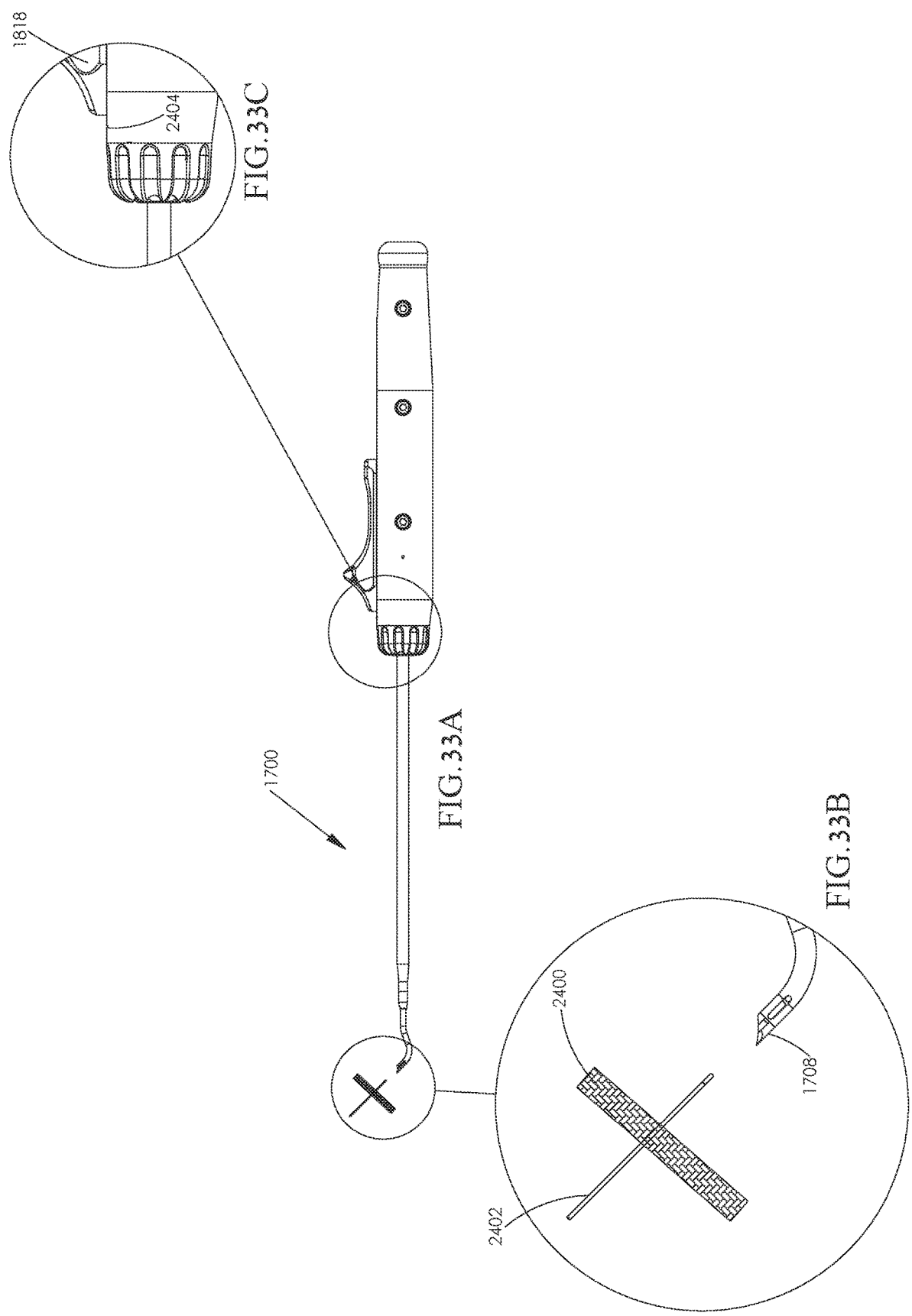

SUTURE CAPTURING DEVICE FOR USE IN ARTHROSCOPIC PROCEDURES

RELATED APPLICATIONS

This application is a National Phase of PCT Patent Application No. PCT/IL2016/050261 having International filing date of Mar. 9, 2016, which claims the benefit of priority under 35 USC § 119(e) of U.S. Provisional Patent Application No. 62/130,040 filed on Mar. 9, 2015. The contents of the above applications are all incorporated by reference as if fully set forth herein in their entirety.

FIELD AND BACKGROUND OF THE INVENTION

The present invention, in some embodiments thereof, relates to suture capturing devices for use in arthroscopic procedures.

Attempts have been made to design suture capturing devices, including the devices described in U.S. Pat. No. 8,585,714 to Weisel, et al., the Pivot NanoPass from Stryker Corporation and the EXPRESSEW® III Flexible Suture Passer from DePuy Synthes.

SUMMARY OF THE INVENTION

There is provided in accordance with an embodiment of the invention, a suture capturing device configured to attain multiple preset orientations, comprising: a handle; a hollow shaft coupled to said handle; a rigid needle element configured with a hook for catching a suture and where the needle element is operatively coupled to the hollow shaft opposite the handle and configured to be slidable in a first direction to assume an open orientation where the hook is exposed relative to the hollow shaft and in a second direction to assume a closed orientation where the hook is not exposed relative to the hollow shaft.

In an embodiment of the invention, the device further comprises a configuration for a partially closed orientation wherein said needle element is placed in an intermediate position between the open and closed orientations such that the hook is not exposed but the needle element is at least partially extended from the hollow shaft.

In an embodiment of the invention, the device further comprises an actuating slide on the handle and operatively connected to the needle element for sliding the needle element distally and proximally.

In an embodiment of the invention, the device further comprises a toothed wheel operatively connected to the needle element where rotation of the wheel effectuates proximal and distal sliding of the needle element.

In an embodiment of the invention, the device further comprises teeth on a bottom of the actuating slide configured as counterparts to the toothed wheel, such that movement of the actuating slide teeth cause movement of the toothed wheel.

In an embodiment of the invention, the device further comprises a tab located in the handle and configured as a counterpart to a notch on a bottom of the actuating slide.

In an embodiment of the invention, the device further comprises an indicator on the top of the handle where when the tab is located in the notch, the front of the actuating slide is positioned at the indicator.

In an embodiment of the invention, the device is configured such that when the front of the actuating slide is positioned at the indicator, the device is in a partially closed orientation.

In an embodiment of the invention, the device further comprises an actuating lever located in the handle and operatively connected to a needle retaining element for displacing the needle element distally relative to said hollow shaft.

In an embodiment of the invention, the device further comprises a locking lever located in the handle and operatively connected to a needle retaining element for displacing the needle element proximally relative to said hollow shaft.

In an embodiment of the invention, the device further comprises a protrusion that a retaining element connected to the locking lever engages to maintain the needle element in a partially closed orientation.

In an embodiment of the invention, the device further comprises a biasing spring in the handle configured to bias the actuating slide in a closed orientation configuration.

In an embodiment of the invention, the device further comprises a biasing spring in the handle configured to bias the needle retaining element in a closed orientation configuration.

In an embodiment of the invention, the needle element is configured with a sharp tip for piercing body tissue.

In an embodiment of the invention, the hollow shaft is rigid.

There is further provided in accordance with an embodiment of the invention, a method for capturing a surgical suture in body tissue using a suture capturing device, comprising: inserting the device into the body tissue in a closed orientation where a hook of a rigid needle tip of the device is covered; transitioning to an open orientation where the hook is uncovered to catch the suture in the hook; changing the device to at least a partially closed orientation after the suture has been captured; and, withdrawing the device from the body tissue.

In an embodiment of the invention, the transitioning is performed by moving an actuating slide in a distal direction.

In an embodiment of the invention, the transitioning is performed by pressing down an actuating lever.

In an embodiment of the invention, the changing is performed by moving the actuating slide in a proximal direction at least to where a tab of the device is located in a notch of the device, with the assistance of a biasing spring.

In an embodiment of the invention, the changing is performed by release of the actuating lever with the assistance of a biasing spring and engaging a protrusion with a retaining element.

In an embodiment of the invention, the method further comprises placing the device in a closed orientation after changing.

In an embodiment of the invention, the method further comprises placing the device in a closed orientation by releasing a locking lever causing the retaining element to release from the protrusion.

There is further provided in accordance with an embodiment of the invention, a method for inserting a surgical suture in body tissue using a suture capturing device, comprising: inserting the device into the body tissue in a closed orientation where a hook of a rigid needle tip of the device is covered and where the suture being inserted is located in the hook; transitioning to an open orientation once the device has been inserted into the body tissue, where the hook is uncovered to release the suture from the hook; changing the device to at least a partially closed orientation after the suture has been released; and, withdrawing the device from the body tissue.

In an embodiment of the invention, the transitioning is performed by moving an actuating slide in a distal direction.

In an embodiment of the invention, the transitioning is performed by pressing down an actuating lever.

In an embodiment of the invention, the changing is performed by moving the actuating slide in a proximal direction at least to where a tab of the device is located in a notch of the device, with the assistance of a biasing spring.

In an embodiment of the invention, the changing is performed by release of the actuating lever with the assistance of a biasing spring and engaging a protrusion with a retaining element.

In an embodiment of the invention, the method further comprises placing the device in a closed orientation after changing.

In an embodiment of the invention, the method further comprises placing the device in a closed orientation by releasing a locking lever causing the retaining element to release from the protrusion.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWING(S)

Some embodiments of the invention are herein described, by way of example only, with reference to the accompanying drawings. With specific reference now to the drawings in detail, it is stressed that the particulars shown are by way of example, not necessarily to scale and for purposes of illustrative discussion of embodiments of the invention. In this regard, the description taken with the drawings makes apparent to those skilled in the art how embodiments of the invention may be practiced.

In the drawings:

FIGS. 2A and 2B are a respective simplified pictorial and side view of a handle element of the suture capturing device of FIG. 1, according to some embodiments of the invention;

FIGS. 3A and 3B are simplified pictorial and side views, respectively, of a retaining element of the suture capturing device of FIG. 1, according to some embodiments of the invention;

FIGS. 4A and 4B are simplified pictorial and side views, respectively, of a locking lever of the suture capturing device of FIG. 1, according to some embodiments of the invention;

FIGS. 6B and 6C are a simplified side view and sectional view, respectively, of the connecting element of FIG. 6A, section being taken along lines C-C in FIG. 6B, according to some embodiments of the invention;

FIG. 8A is a simplified pictorial view of an adaptor element of the suture capturing device of FIG. 1, according to some embodiments of the invention;

FIGS. 8B and 8C are a simplified side view and sectional view, respectively, of the adaptor element of FIG. 8A, section being taken along lines C-C in FIG. 8B, according to some embodiments of the invention;

FIGS. 13-16 are simplified assembled view illustrations showing the various steps in the method of operation of the suture capturing device of FIG. 1, according to some embodiments of the invention;

FIGS. 24A-24C show a device of FIG. 17 in a closed orientation for insertion into body tissue without a suture, in accordance with an exemplary embodiment of the invention;

FIGS. 25A-25C show a device of FIG. 17 inserted into the body and in an open orientation for catching a suture, in accordance with an exemplary embodiment of the invention;

FIGS. 26A-26C show a device of FIG. 17 inserted into the body and in a partially closed orientation with a caught suture, in accordance with an exemplary embodiment of the invention;

FIGS. 27A-27C show a device of FIG. 17 in a closed orientation for withdrawal from the body and withdrawn from the body, in accordance with an exemplary embodiment of the invention;

FIGS. 28A-28C show a device of FIG. 17 in an open operative orientation for releasing the suture outside the body, in accordance with an exemplary embodiment of the invention;

FIGS. 29A-29C show a device of FIG. 17 in a closed orientation for insertion of a suture into a body, in accordance with an exemplary embodiment of the invention;

FIGS. 31A-31C show a device of FIG. 17 inserted into the body and in a partially closed orientation with a caught suture, in accordance with an exemplary embodiment of the invention;

FIGS. 32A-32C show a device of FIG. 17 in an open orientation and releasing a suture, in accordance with an exemplary embodiment of the invention;

FIGS. 33A-33C show a device of FIG. 17 withdrawn from the body in a closed orientation and leaving a suture in the body, in accordance with an exemplary embodiment of the invention;

DESCRIPTION OF SPECIFIC EMBODIMENTS OF THE INVENTION

Figure 1:
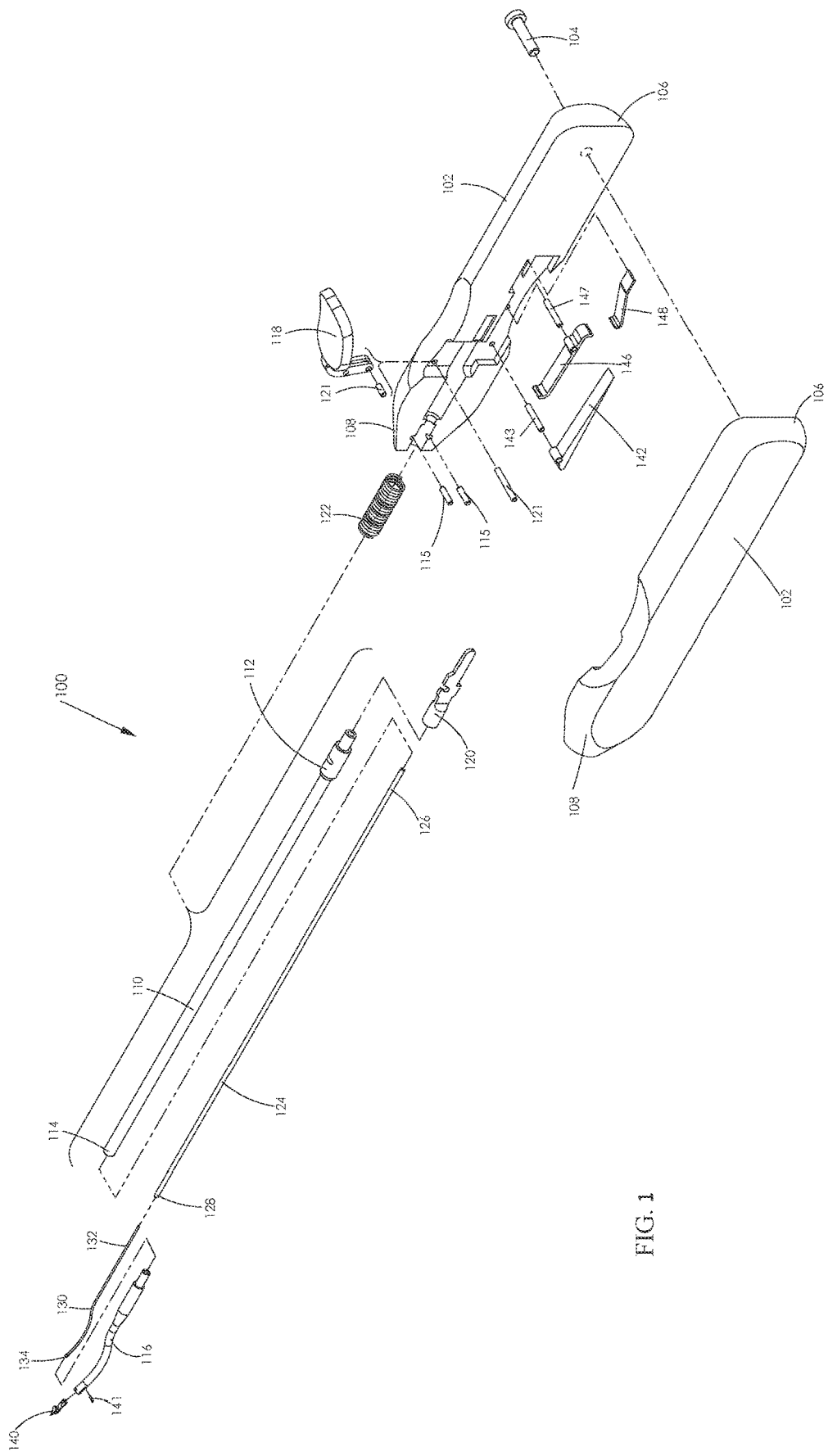
FIG. 1 is a simplified exploded view illustration of a suture capturing device constructed and operative in accordance with some embodiments of the present invention.

The present invention, in some embodiments thereof, relates to suture capturing devices for use in arthroscopic procedures.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

Reference is now made to FIG. 1, which is a simplified exploded view illustration of a suture capturing device constructed and operative in accordance with some embodiments of the present invention.

It is seen in FIG. 1 that a suture capturing device 100 includes a handle element 102, which has two generally identical halves which are attached using a connection pin 104, according to some embodiments. Alternatively, in some embodiments the two halves of the handle element 102 can be connected using any other method such as welding or attachment by adhesive or by screw, as examples. The handle element 102 has a proximal end 106 and a distal end 108.

A hollow shaft 110 has a proximal end 112 and a distal end 114. The proximal end 112 of the hollow shaft 110 is coupled with and, in some embodiments, at least partially inserted into the distal end 108 of handle element 102, optionally using connecting pins 115. In some embodiments, an adaptor element 116 is coupled to or, in some embodiments, integrally made with the hollow shaft 110. It is appreciated that adaptor element 116 can be formed in various shapes and angles in order to fit various anatomical locations.

In some embodiments, an actuating lever 118 is partially inserted between the two halves of handle element 102 and is coupled to the proximal end 112 of hollow shaft 110, optionally using a connecting element 120. In some embodiments, the actuating lever 118 is coupled to handle element 102 using connecting pins 121.

It is also seen that in some embodiments, a biasing spring 122 is provided. In some embodiments, the spring is inserted into the distal end 108 of handle element 102 and optionally at least partially encircles the connecting element 120 and/or the proximal end 112 of the hollow shaft 110.

In some embodiments, a needle retaining element 124 extends within hollow shaft 110 and has a proximal end 126 and a distal end 128. In some embodiments, the proximal end 126 of the needle retaining element 124 is coupled to connecting element 120. In some embodiments, the distal end 124 of the needle retaining element 124 is coupled to or, in some embodiments, integrally made with a needle retaining element adaptor 130 having a proximal end 132 and a distal end 134. In some embodiments, the proximal end 132 of needle retaining element adaptor 130 is coupled to the needle retaining element 124 and the distal end 134 of needle retaining element adaptor 130 is coupled to a needle element 140, optionally using a connecting pin 141.

In some embodiments, a locking lever 142 is hingedly coupled, optionally using a connecting pin 143 to the handle element 102. In some embodiments, a retaining element 146 is hingedly coupled to handle element 102, optionally using a connecting pin 147 and is generally supported on the locking lever 142. In some embodiments, the retaining element 146 is biased to its initial position by a leaf spring 148, which is optionally fixedly locked to a notch formed in handle element 102 at one side and is supported on retaining element 146 on the other side.

Reference is now made to FIGS. 2A and 2B, which are a respective simplified pictorial and side view of the handle element of the suture capturing device 100 of FIG. 1, according to some embodiments.

As noted hereinabove, in some embodiments the handle element 102 has two generally identical halves which are attached using a connection pin 104. The handle element 102 has proximal end 106 and distal end 108.

It is seen in FIGS. 2A and 2B that handle element 102 is arranged along a longitudinal axis 160. In some embodiments, the outer surface of handle element 102 is formed with gripping surfaces 162.

In some embodiments, a generally semi-circular groove 164 is formed at the distal end 108 of handle element 102 and extends proximally from distal end 108 for insertion of the proximal end 112 of the hollow shaft 110 therethrough.

In some embodiments, a plurality of recesses 166 are formed within groove 164 for engagement with connecting pins 115.

In some embodiments, a longitudinal recess 168 is formed within handle 102 and extends proximally from groove 164 for insertion of the connecting element 120 therein.

In some embodiments, a generally rectangular recess 170 is formed adjacent the longitudinal recess 168 for insertion of the activation lever 118 therein. Optionally, a recess 172 is formed in rectangular recess 170 for engagement with connecting pin 121.

In some embodiments, an additional recess 174 is formed within handle 102 and is located adjacent recess 168 and extends generally proximally therefrom. In some embodiments, recess 174 is configured to encompass the locking lever 142, the retaining element 146 and leaf spring 148 therewithin. Optionally, recesses 176 and 178 are formed in recess 174 to engage with connecting pins 143 and 147 respectively.

In some embodiments, a notch 180 is formed adjacent and above the proximal end of recess 174 for retaining an end of the leaf spring 148 therein.

It is also seen in FIGS. 2A and 2B that in some embodiments, recesses 182 are formed in handle element 102 and are longitudinally spaced from each other for engagement with connection pins 104 in order to connect the two halves of the handle element 102.

Reference is now made to FIGS. 3A and 3B, which are a respective simplified pictorial and side view of the retaining element 146 of the suture capturing device 100 of FIG. 1, according to some embodiments.

In some embodiments, retaining element 146 is formed of a generally planar longitudinal portion 188 arranged along a longitudinal axis 189, the longitudinal portion 188 having a proximal end 190 and a distal end 192 each of which has a curved portion 194 and 196 respectively. In some embodiments, curved portion 196 is directed generally upwardly with respect to planar longitudinal portion 188 and curved portion 194 is directed generally downwardly with respect to planar longitudinal portion 188.

In some embodiments, a protrusion 198 is formed adjacent the proximal end 190 of retaining element 146 and is arranged along an axis transverse to longitudinal axis 189. In some embodiments, an opening 200 is formed within protrusion 198 and extends along the axis that is transverse to longitudinal axis 189. Optionally, opening 200 is provided to enable insertion of connection pin 147 therethrough and connection thereof with handle element 102, thus providing for hinged engagement of retaining element 146 with handle element 102.

Reference is now made to FIGS. 4A and 4B, which are a respective simplified pictorial and side view of locking lever 142 of the suture capturing device 100 of FIG. 1, according to some embodiments.

In some embodiments, locking lever 142 is formed of a generally longitudinal distally tapered portion 202 and is arranged along a longitudinal axis 203, which has a proximal end 204 and a distal end 206.

In some embodiments, a protrusion 208 is formed adjacent the distal end 206 of locking lever 142 and is arranged along an axis transverse to longitudinal axis 203. In some embodiments, an opening 210 is formed within protrusion 208 and extends along the axis that is transverse to longitudinal axis 203. Optionally, opening 210 is provided to enable insertion of connection pin 143 therethrough and connection thereof with handle element 102, thus providing for hinged engagement of locking lever 142 with handle element 102.

Figure 5A:
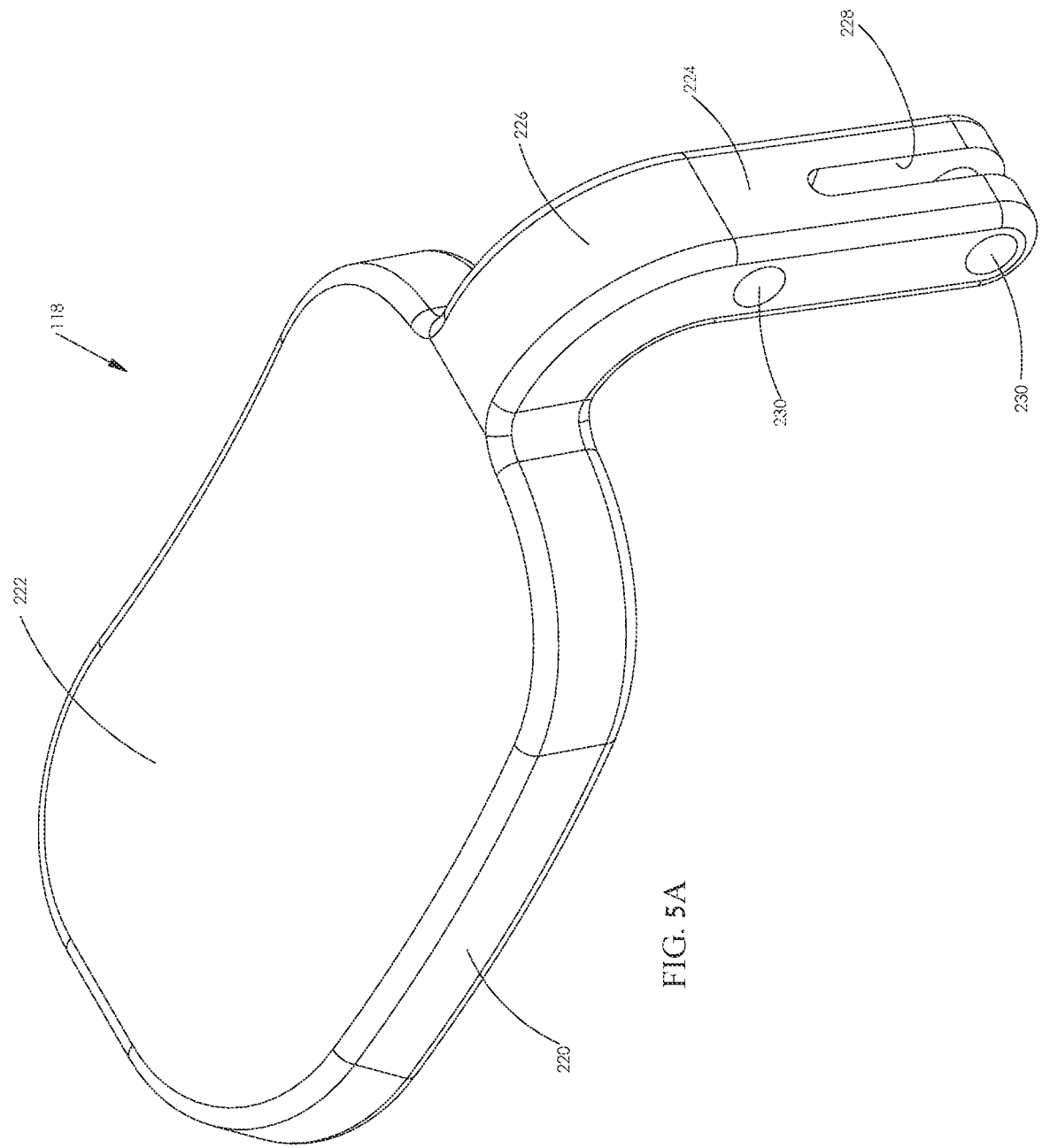
FIG. 5A is a simplified pictorial view of an actuating lever of the suture capturing device of FIG. 1, according to some embodiments of the invention.
Figure 5C:
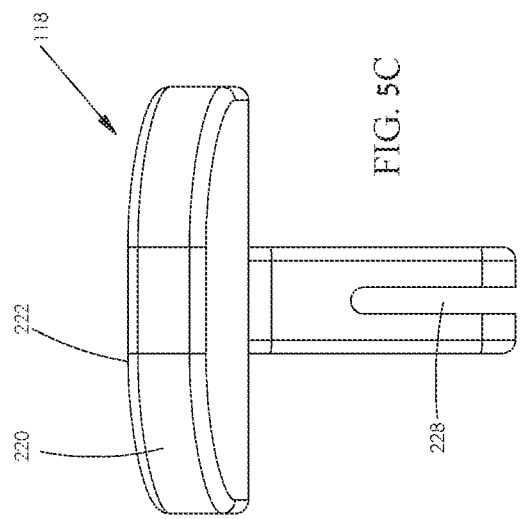
FIGS. 5B-5D are a simplified side view, front view and top view, respectively, of the actuating lever of FIG. 5A, according to some embodiments of the invention.
Figure 5B:
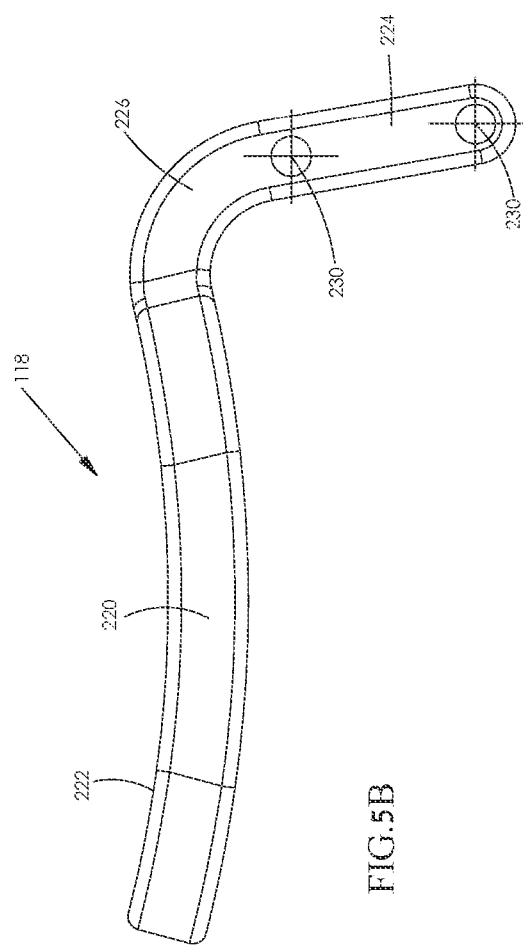
Figure 5D:
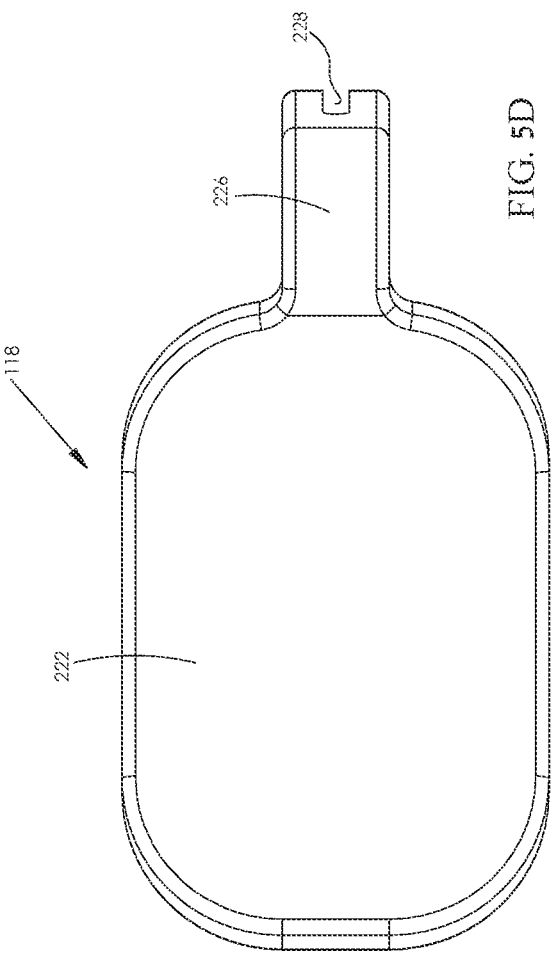

Reference is now made to FIG. 5A, which is a simplified pictorial view of the actuating lever 118 of the suture capturing device 100 of FIG. 1 and to FIGS. 5B-5D, which are a respective simplified side view, front view and top view of the actuating lever 118 of FIG. 5A, according to some embodiments.

In some embodiments, actuating lever 118 has a generally planar portion 220 with an ergonomic pressing surface 222 and a generally longitudinal portion 224 extending generally perpendicularly to planar portion 220 and joined thereto by a curved portion 226.

In some embodiments, a notch 228 is formed along a portion of the longitudinal portion 224 for engagement with connecting portion 120.

It is additionally seen in FIGS. 5A and 5B that in some embodiments, two openings 230 are formed through the longitudinal portion 224 and extend transversely thereto. Optionally, openings 230 are provided for insertion of connecting pins 121 thereto in order to enable pivoting displacement of the actuating lever 118 relative to handle element 102.

Figure 6A:
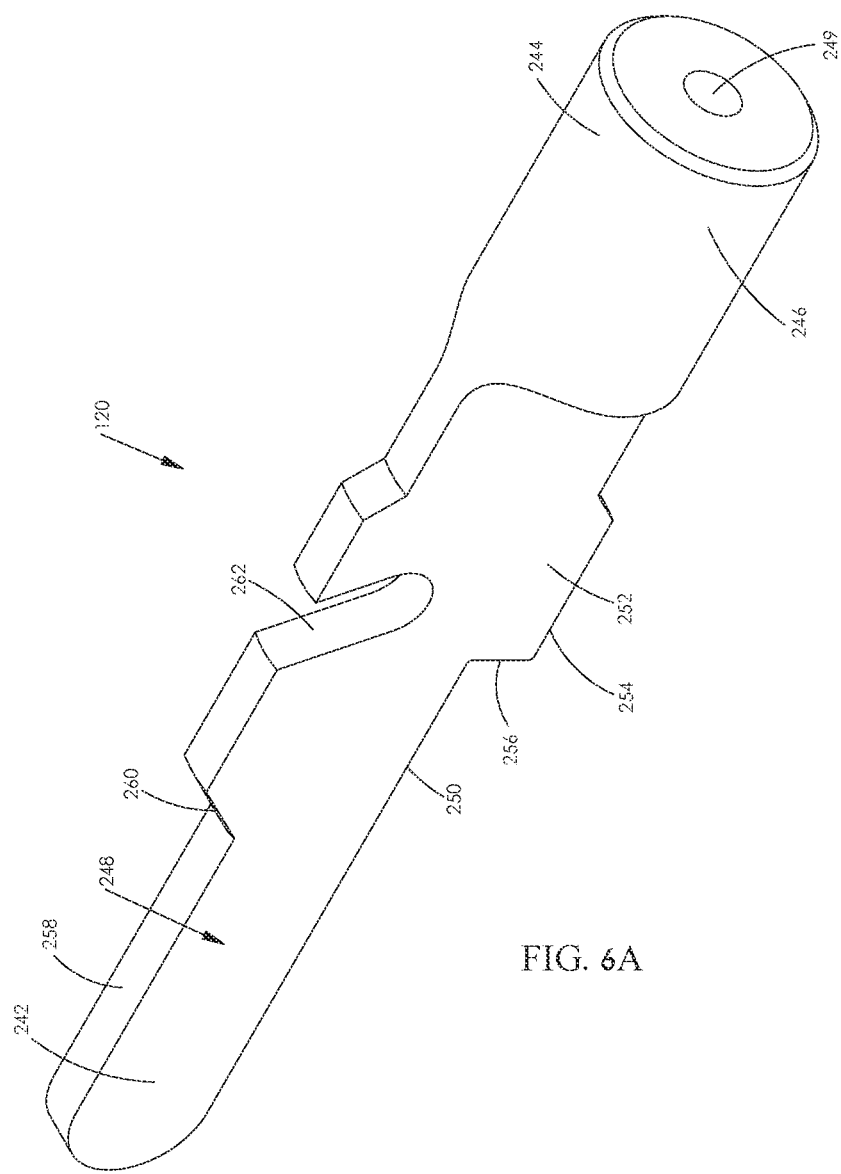
FIG. 6A is a simplified pictorial view of a connecting element of the suture capturing device of FIG. 1, according to some embodiments of the invention.

Reference is now made to FIG. 6A, which is a simplified pictorial view of the connecting element 120 of the suture capturing device 100 of FIG. 1 and to FIGS. 6B and 6C, which are a respective simplified side view and sectional view of the connecting element 120 of FIG. 6A, section being taken along lines C-C in FIG. 6B, according to some embodiments.

In some embodiments, connecting element 120 is a generally longitudinal element arranged along a longitudinal axis 240 and has a proximal end 242 and a distal end 244. Extending proximally from the distal end 244 is a generally cylindrical portion 246, which is adapted for insertion into handle element 102. In some embodiments, a longitudinal recess 249 is formed along cylindrical portion 246 for insertion of a connecting pin which provides for connection of the connecting element 120 and the hollow shaft 110.

It is also seen in FIGS. 6A-6C that, in some embodiments, extending proximally from the cylindrical portion 246 is a generally planar portion 248 which is inserted into handle element 102 and is optionally fixedly locked between its two halves.

In some embodiments, the planar portion 248 defines a downwardly facing wall surface 250 extending distally from proximal end 242 and a protrusion 252 extending downwardly from wall surface 250. In some embodiments, protrusion 252 defines a downwardly facing wall surface 254 and a proximally facing shoulder 256. Optionally, downwardly facing wall surface 254 is located downwardly and generally in parallel to downwardly facing wall surface 250.

In some embodiments, the planar portion 248 defines an upwardly facing wall surface 258 extending distally from proximal end 242 extending distally to a distally tapered surface 260 and having a distally tapered notch 262 formed in planar portion 248, the notch 262 is located proximally to tapered surface 260. In some embodiments, the notch 262 is provided for engagement with connecting pin 121 in order to enable pivoting displacement of actuating lever 118 relative to connecting element 120.

Figure 7A:
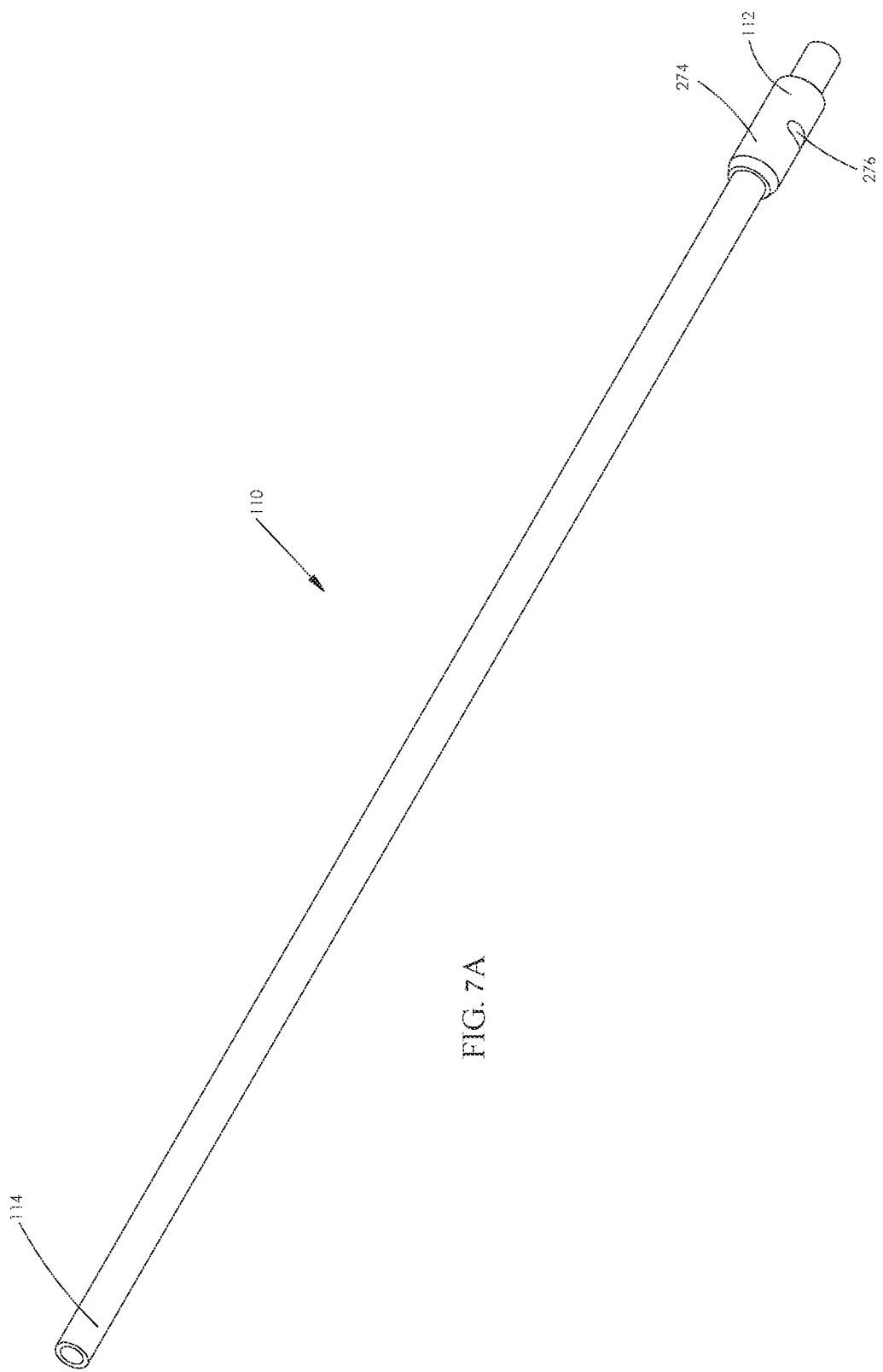
FIG. 7A is a simplified pictorial view of a hollow shaft of the suture capturing device of FIG. 1, according to some embodiments of the invention.
Figure 7C:
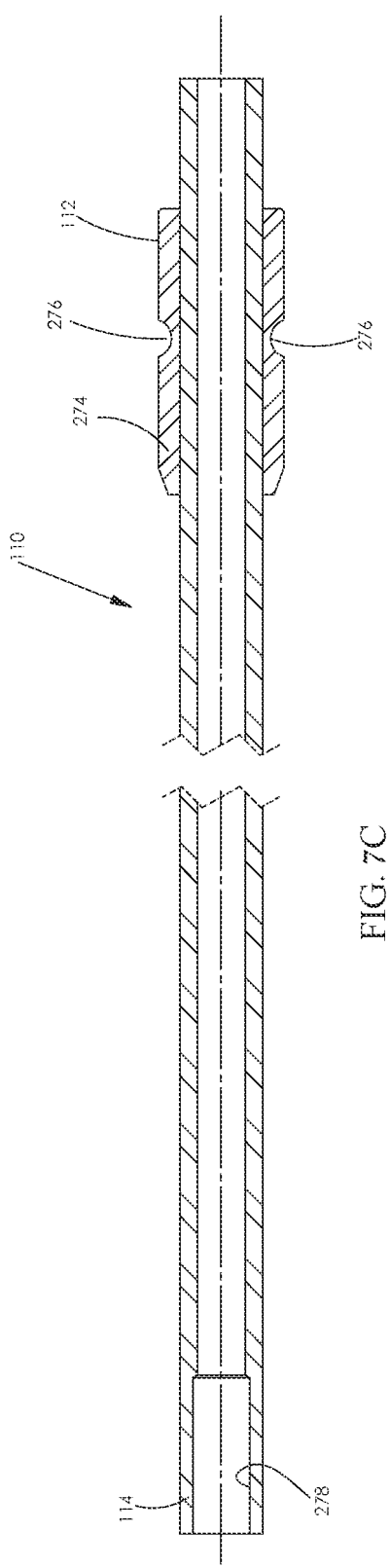
FIGS. 7B and 7C are a simplified side view and sectional view, respectively, of the hollow shaft of FIG. 7A, section being taken along lines C-C in FIG. 7B, according to some embodiments of the invention.
Figure 7B:
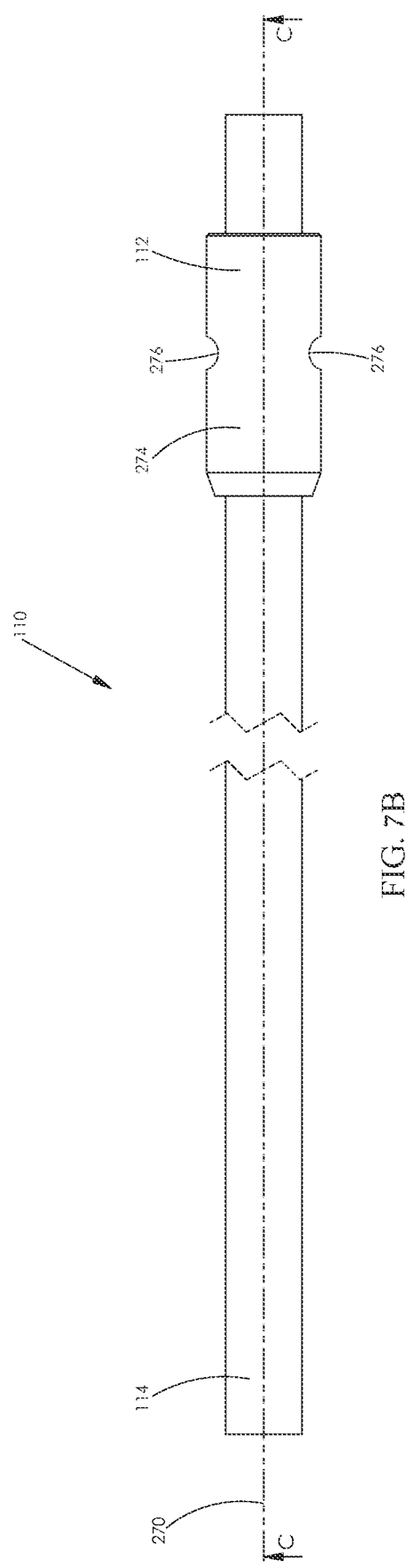

Reference is now made to FIG. 7A, which is a simplified pictorial view of the hollow shaft 110 of the suture capturing device 100 of FIG. 1 and to FIGS. 7B and 7C, which are a respective simplified side view and sectional view of the hollow shaft 110 of FIG. 7A, section being taken along lines C-C in FIG. 7B, according to some embodiments.

In some embodiments, hollow shaft 110 is formed as a generally cylindrical element having proximal end 112 and distal end 114 as noted hereinabove. Optionally, hollow shaft is generally formed as an integral element made of a rigid material, such as for example Titanium or any other biocompatible material and is generally arranged along a longitudinal axis 270. In some embodiments, a relatively widened portion 274 is either integrally formed or coupled to the hollow shaft 110 and located adjacent proximal end 112 of hollow shaft 110. In some embodiments, a plurality of notches 276 are formed on widened portion 274 for engagement with connecting pins 115 in order to connect hollow shaft 110 with handle element 102.

In some embodiments, an inner socket 278 is formed within hollow shaft 110 and extending proximally from distal end 114 thereof, provided for engagement and connection of the hollow shaft 110 and the adaptor element 116.

Reference is now made to FIG. 8A, which is a simplified pictorial view of the adaptor element 116 of the suture capturing device 100 of FIG. 1 and to FIGS. 8B and 8C, which are a respective simplified side view and sectional view of the adaptor element 116 of FIG. 8A, section being taken along lines C-C in FIG. 8B, according to some embodiments.

As noted hereinabove, adaptor element 116 is, in some embodiments, coupled to or integrally made with the hollow shaft 110. It is appreciated that adaptor element 116 can be formed in various shapes and angles in order to fit various anatomical locations.

In some embodiments, adaptor element 116 is formed as a generally hollow longitudinal element having a proximal end 290 and a distal end 292. Optionally, a relatively narrow shaft 294 is formed at the proximal end 290 of adaptor element 116 to enable connection of adaptor element 116 and hollow shaft 110.

In some embodiments, two longitudinal apertures 296 are formed at the distal end 292 of adaptor element 116 for engagement with connecting pin 141, this engagement provides for longitudinal displacement of needle element 140 relative hollow shaft 110 as will be described in detail hereinbelow.

It is additionally seen in FIGS. 8A and 8C that in some embodiments two recesses 298 are formed along the circumference of the distal end 292 of adaptor element 116 for engagement with needle element 140. It is appreciated that in some embodiments recesses 298 of adaptor element 116 are formed with a rounded edge in order to protect the integrity of a surgical suture when it is captured between the adaptor element 116 and the needle element 140.

Figure 9A:
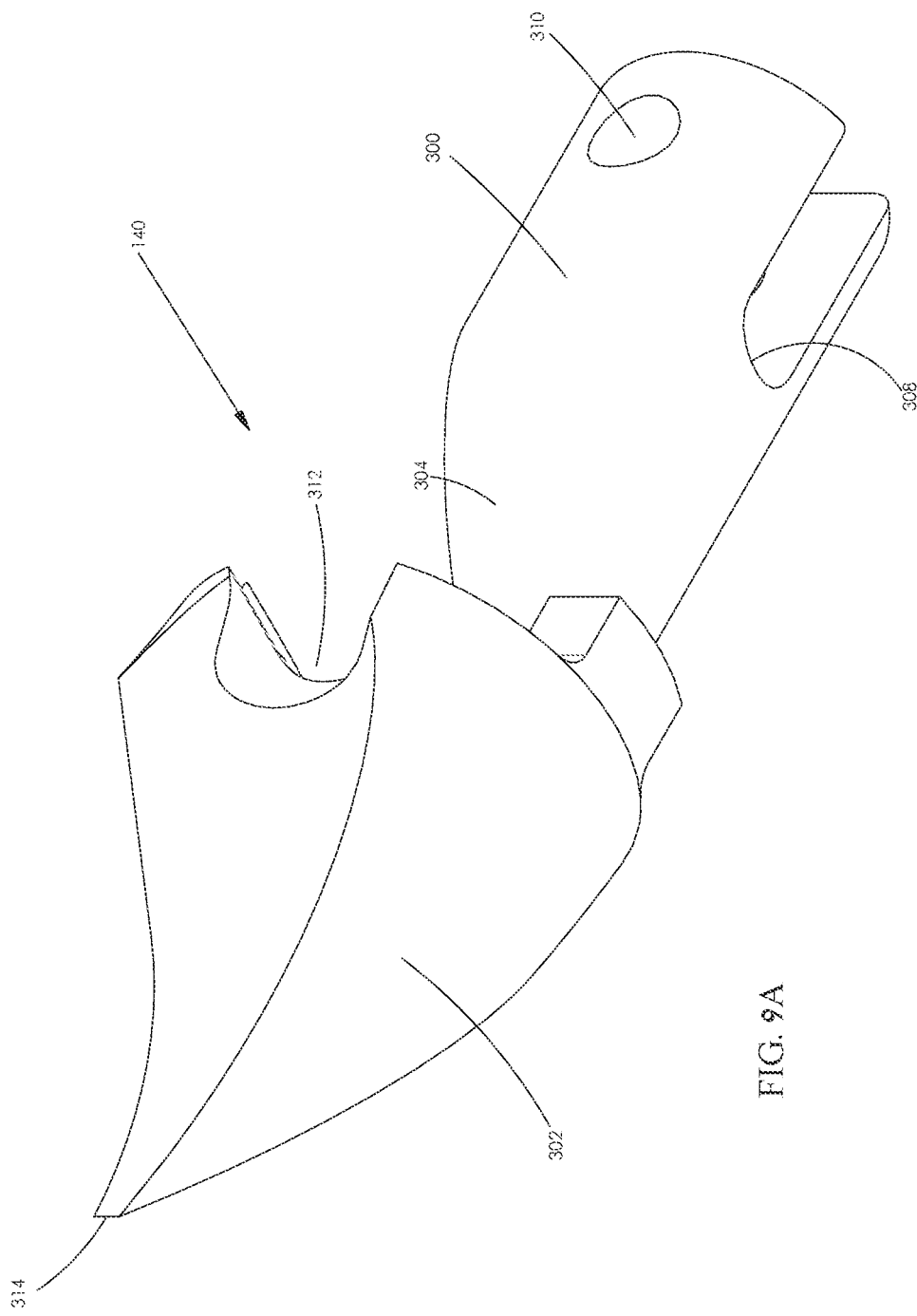
FIG. 9A is a simplified pictorial view of a needle element of the suture capturing device of FIG. 1, according to some embodiments of the invention.
Figure 9F:
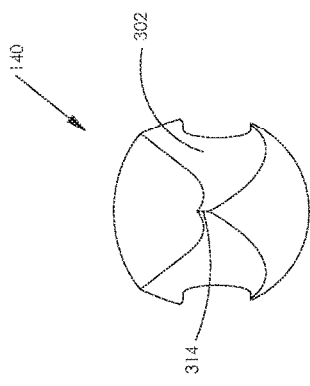
FIGS. 9B-9F are various planar view illustrations of the needle element of FIG. 9A, according to some embodiments of the invention.
Figure 9B:
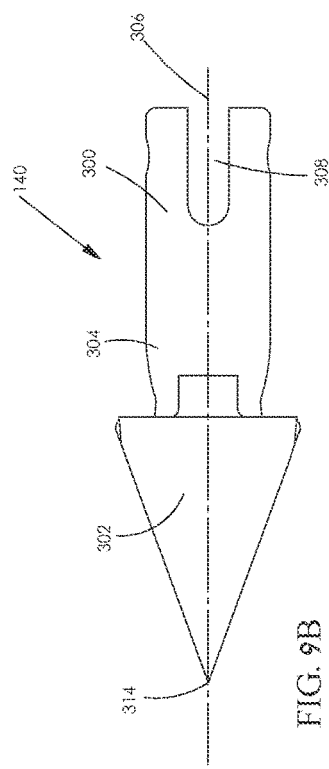
Figure 9C:
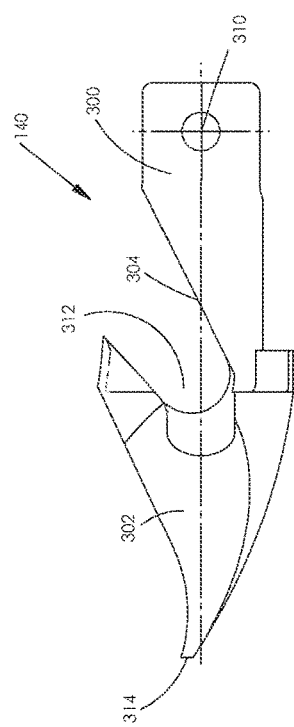
Figure 9D:
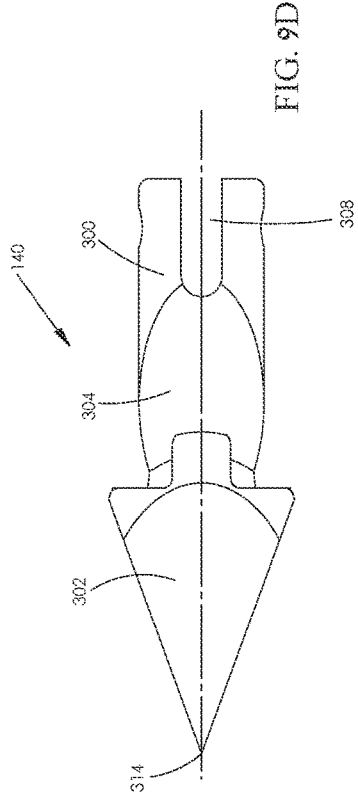
Figure 9E:
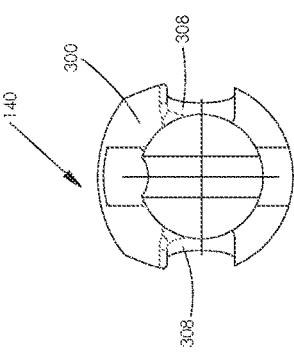

Reference is now made to FIG. 9A, which is a simplified pictorial view of the needle element 140 of the suture capturing device 100 of FIG. 1 and to FIGS. 9B-9F, which are various planar view illustrations of the needle element 140 of FIG. 9A, according to some embodiments.

In some embodiments, needle element 140 has a proximal generally cylindrical portion 300, a distal needle-shaped portion 302 and a curved joining portion 304. In some embodiments, needle element 140 is generally formed as an integral element made of a rigid (non-flexible) material, such as for example Titanium or any other biocompatible material and is generally arranged along a longitudinal axis 306.

In some embodiments, a generally longitudinal opening 308 is formed at the proximal end of cylindrical portion 300 and extend distally therefrom. Optionally, a through opening 310 is formed at the proximal end of cylindrical portion 300 extending transversely to longitudinal axis 306. In some embodiments, openings 308 and 310 are formed in the needle element 140 for enabling connection of the needle element 140 with the needle retaining element adaptor 130 and in turn with needle retaining element 124 and in turn with connecting element 120.

In some embodiments, curved joining portion 304 defines an inclined generally U-shaped recess 312, forming a hook-like structure, for accommodating a surgical suture therein. Needle shaped portion 302 defines a sharp tip 314 for penetration of tissue.

Figure 10:
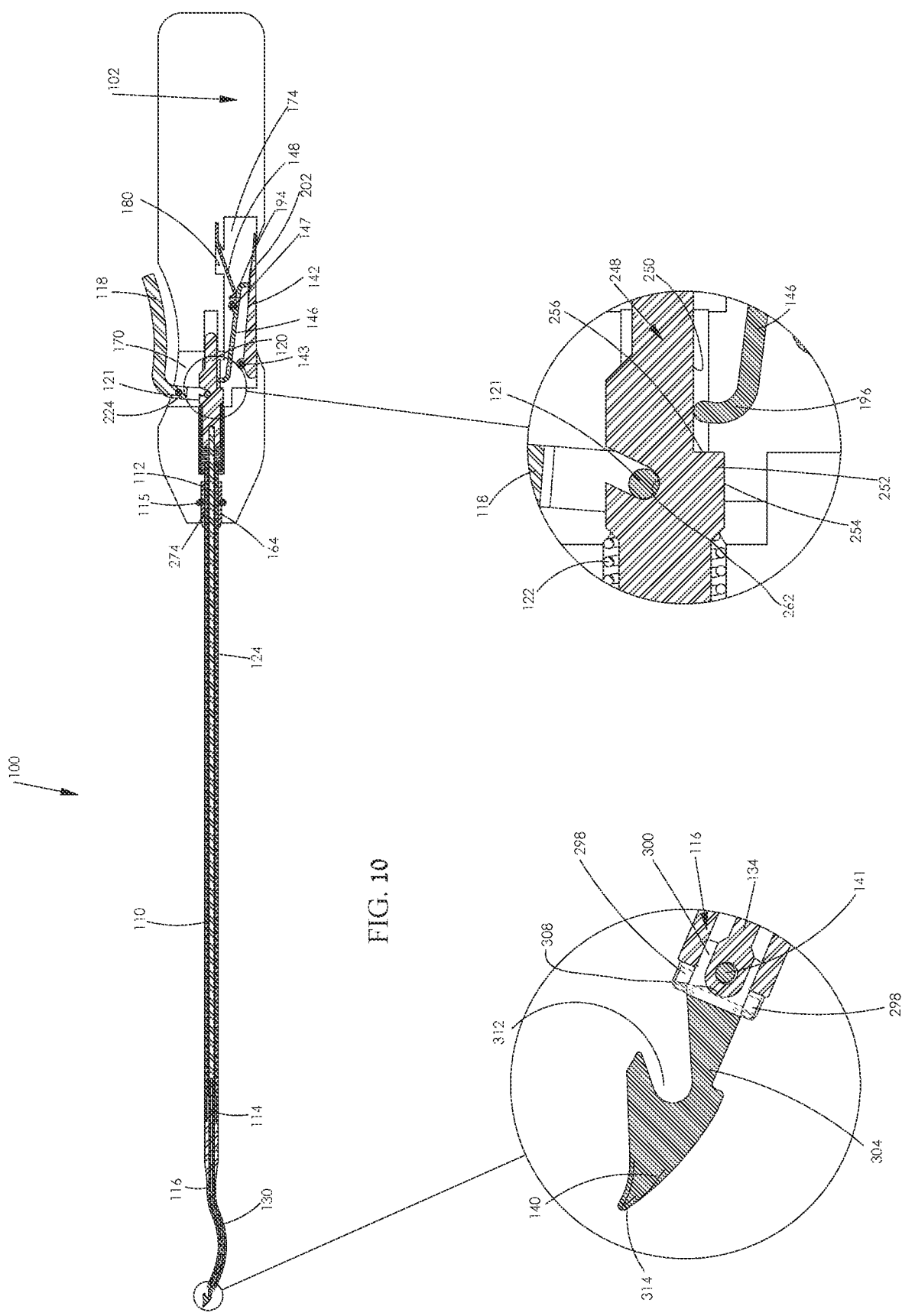
FIG. 10 is a simplified assembled view illustration of the suture capturing device of FIG. 1 shown in an open operative orientation, according to some embodiments of the invention.

Reference is now made to FIG. 10, which is a simplified assembled view illustration of the suture capturing device 100 of FIG. 1 shown in an open operative orientation, according to some embodiments.

It is seen in FIG. 10 that in some embodiments connecting element 120 is inserted into handle element 102, specifically cylindrical portion 246 of the connecting element 120 is inserted into longitudinal recess 168 of handle element 102. In some embodiments, the actuating lever 118 is partially inserted into handle element 102 and is engaged with the connecting element 120, such that planar portion 248 of the connecting element 120 is inserted through notch 228 of the actuating lever 118 and the connecting pin 121 is seated within notch 262 of the connecting element 120, thus providing for a sliding movement of the connecting element 120 relative handle element 102 along longitudinal axis, such as for example axis 240. In some embodiments, biasing spring 122 is seated in recess 168 of handle element 102 and supported against connecting element 120.

In some embodiments, hollow shaft element 110 is partially inserted into handle element 102, namely the proximal end 112 of the hollow shaft element 110 is inserted into semi-circular groove 164 of handle element 102 and is optionally fixedly held therewithin by engagement of connecting pins 115 with notches 276 of hollow shaft 110 and recesses 166 of groove 164 of handle element 102.

In some embodiments, adaptor element 116 is fixedly connected to hollow shaft 110 or integrally made therewith.

In some embodiments, needle retaining element 124 is fixedly inserted within connecting element 120, such that proximal end 126 of needle retaining element 124 is inserted into longitudinal recess 248 of connecting element 120. In some embodiments, needle retaining element adaptor 130 is fixedly coupled to needle retaining element 124. Optionally, needle element 140 is in turn connected to needle retaining element adaptor 130 by means of engagement with connecting pins 141. Optionally, the connecting pins 141 are slidable within longitudinal apertures 296 of adaptor element 116.

It is a particular feature of some embodiments of the present invention that the sliding movement of the connecting element 120 is transferred to needle retaining element 124, in turn to needle retaining element adaptor 130 and finally to needle element 140. In some embodiments, due to this transfer and to the fact that connecting pins 141 are slidable within longitudinal apertures 296 of adaptor element 116, relative axial movement is provided between needle element 140 and the distal end 292 of adaptor element 116.

In some embodiments, locking lever 142 is hingedly connected to handle element 102 by means of connecting pin 143. In some embodiments, retaining element 146 is hingedly connected to handle element 102 by means of connecting pin 147 and is enclosed within handle element 102 by means of locking lever 142. In some embodiments, leaf spring 148 is fixedly inserted into notch 180 of handle element 102 and biases retaining element 146 to engage locking lever 142 with curved portion 194 and further engage downwardly facing wall surface 250 of connecting element 120 with curved portion 196 thereof, adjacent to but not touching proximally facing shoulder 256 of connecting element 120.

It is a particular feature of some embodiments of the present invention that in an open operative orientation of the suture capturing device 100 the actuating lever 118 is pressed down, the connecting element 120 is displaced distally, the biasing spring 122 is compressed and the needle element 140 is located distally with respect to distal end 292 of adaptor element 116 and thus providing U-shaped recess 312 of the needle element 140 for capturing a surgical suture therewithin.

Figure 11:
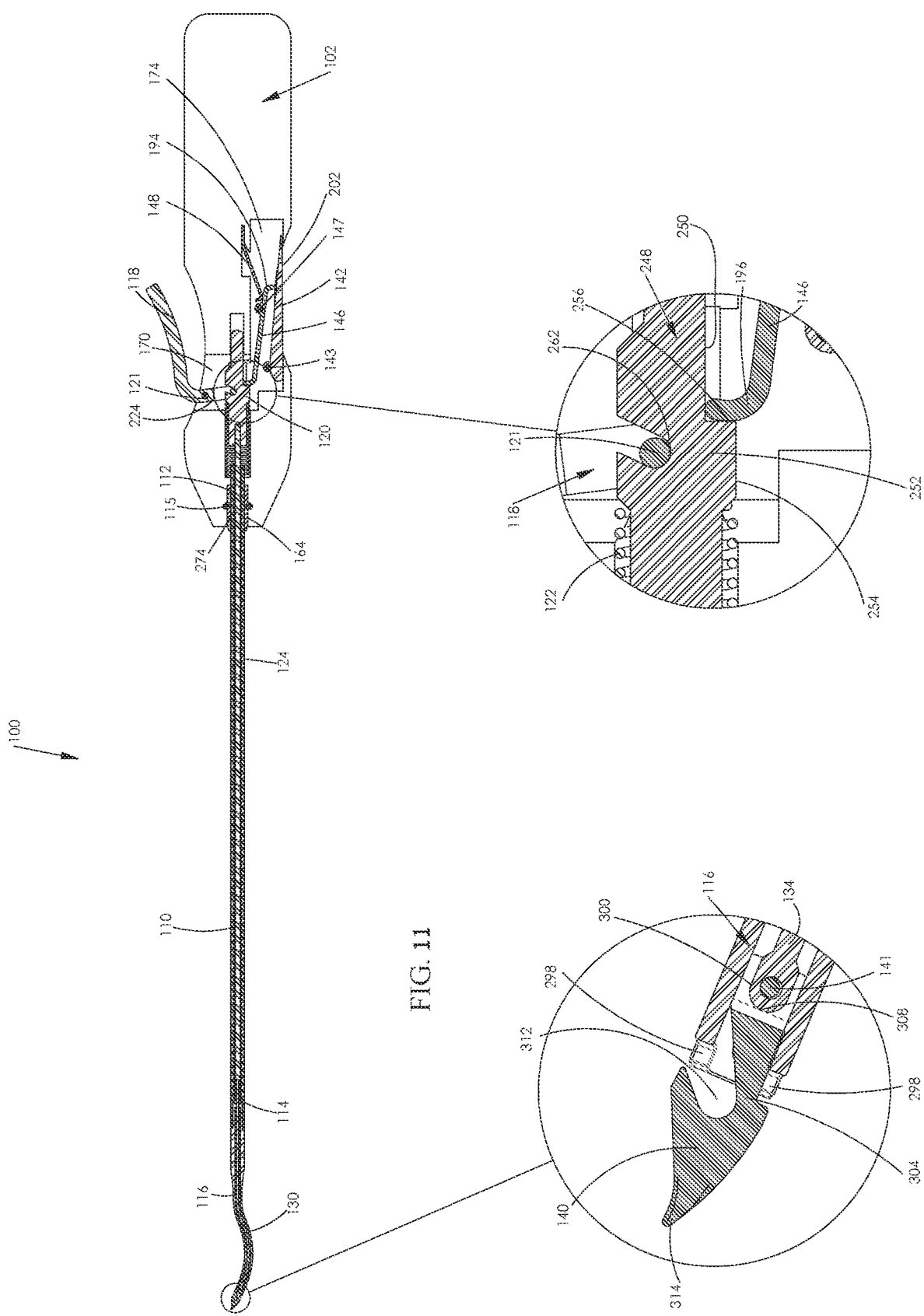
FIG. 11 is a simplified assembled view illustration of the suture capturing device of FIG. 1 shown in a partially closed operative orientation, according to some embodiments of the invention.

Reference is now made to FIG. 11, which is a simplified assembled view illustration of the suture capturing device 100 of FIG. 1 shown in a partially closed operative orientation, according to some embodiments.

It is seen in FIG. 11 that in some embodiments, connecting element 120 remains inserted into handle element 102, specifically cylindrical portion 246 of the connecting element 120 is inserted into longitudinal recess 168 of handle element 102. In some embodiments, the actuating lever 118 remains partially inserted into handle element 102 and is engaged with the connecting element 120, such that planar portion 248 of the connecting element 120 is inserted through notch 228 of the actuating lever 118 and the connecting pin 121 is seated within notch 262 of the connecting element 120, thus providing for a sliding movement of the connecting element 120 relative handle element 102 along longitudinal axis, such as for example axis 240. In some embodiments, biasing spring 122 is seated in recess 168 of handle element 102 and supported against connecting element 120.

In some embodiments, hollow shaft element 110 remains partially inserted into handle element 102, namely the proximal end 112 of the hollow shaft element 110 is inserted into semi-circular groove 164 of handle element 102 and optionally fixedly held therewithin by engagement of connecting pins 115 with notches 276 of hollow shaft 110 and recesses 166 of groove 164 of handle element 102.

In some embodiments, adaptor element 116 remains fixedly connected to hollow shaft 110 or integrally made therewith.

In some embodiments, needle retaining element 124 remains fixedly inserted within connecting element 120, such that proximal end 126 of needle retaining element 124 is inserted into longitudinal recess 248 of connecting element 120. Needle retaining element adaptor 130 remains fixedly coupled to needle retaining element 124. Needle element 140 remains in turn connected to needle retaining element adaptor 130 by means of engagement with connecting pins 141. Optionally, the connecting pins 141 are slidable within longitudinal apertures 296 of adaptor element 116.

It is a particular feature of some embodiments of the present invention that the sliding movement of the connecting element 120 is transferred to needle retaining element 124, in turn to needle retaining element adaptor 130 and finally to needle element 140. Optionally, due to this transfer and to the fact that connecting pins 141 are slidable within longitudinal apertures 296 of adaptor element 116, relative axial movement is provided between needle element 140 and the distal end 292 of adaptor element 116.

In some embodiments, locking lever 142 remains hingedly connected to handle element 102 by means of connecting pin 143. In some embodiments, retaining element 146 remains hingedly connected to handle element 102 by means of connecting pin 147 and is enclosed within handle element 102 by means of locking lever 142. In some embodiments, leaf spring 148 remains fixedly inserted into notch 180 of handle element 102 and biases retaining element 146 to engage locking lever 142 with curved portion 194 and further engage downwardly facing wall surface 250 of connecting element 120 with curved portion 196 thereof, adjacent and supported against proximally facing shoulder 256 of connecting element 120, thus causing the biasing spring 122 to remain partially compressed.

It is a particular feature of some embodiments of the present invention that in a partially closed operative orientation of the suture capturing device 100 the actuating lever 118 is slightly lifted upwards, the connecting element 120 is displaced slightly proximally, the biasing spring 122 is partially compressed and the needle element 140 is located distally with respect to distal end 292 of adaptor element 116 but nearly touching distal end 292 and thus providing U-shaped recess 312 of the needle element 140 for fixedly holding the surgical suture between the needle element 140 and the distal end 292 and prevent the surgical suture from disengagement therefrom, however allows for movement of the surgical suture therewithin.

Figure 12:
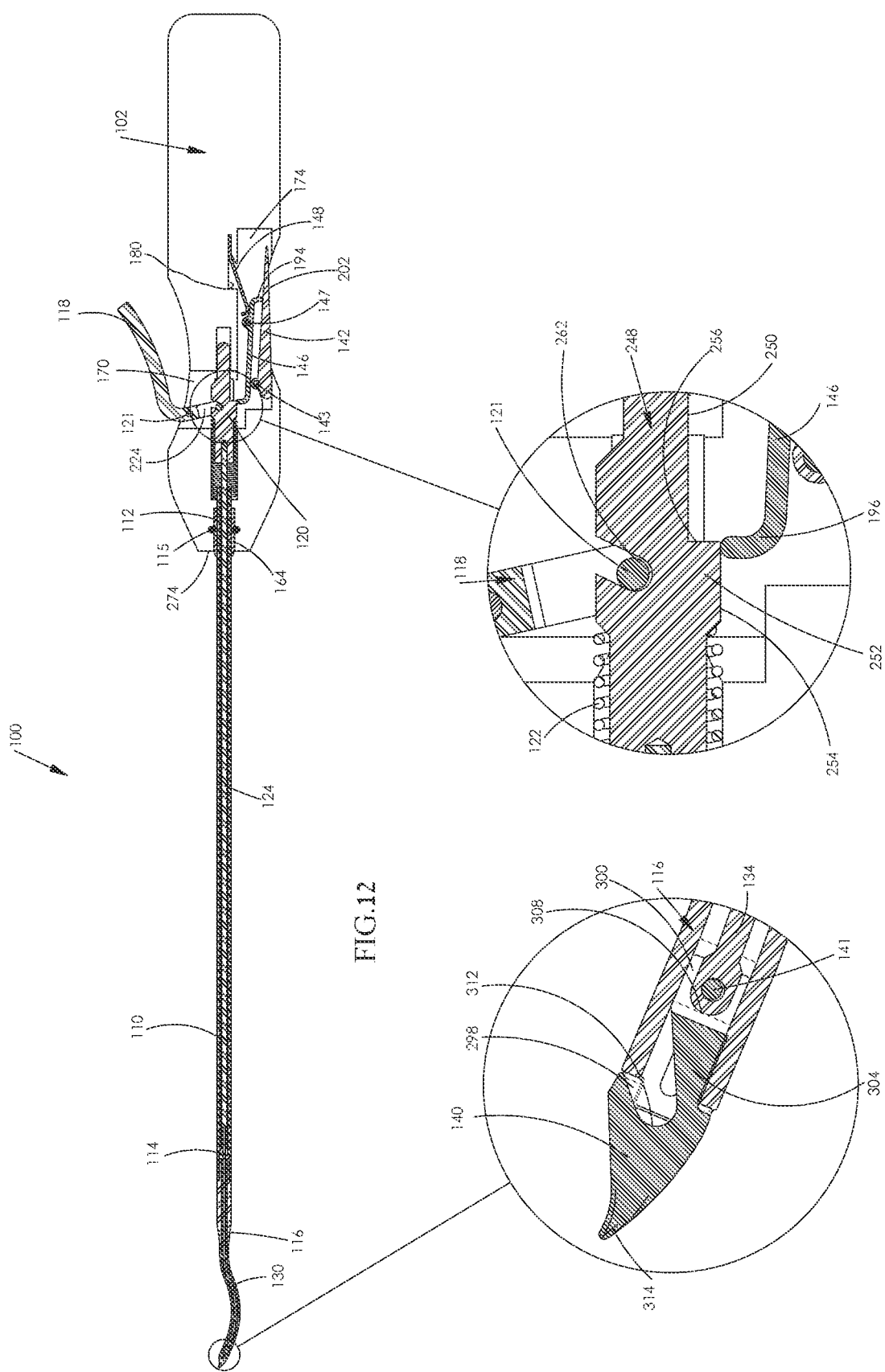
FIG. 12 is a simplified assembled view illustration of the suture capturing device of FIG. 1 shown in a closed operative orientation, according to some embodiments of the invention.

Reference is now made to FIG. 12, which is a simplified assembled view illustration of the suture capturing device 100 of FIG. 1 shown in a closed operative orientation, according to some embodiments.

It is seen in FIG. 12 that in some embodiments, connecting element 120 remains inserted into handle element 102, specifically cylindrical portion 246 of the connecting element 120 is inserted into longitudinal recess 168 of handle element 102. In some embodiments, the actuating lever 118 remains partially inserted into handle element 102 and is engaged with the connecting element 120, such that planar portion 248 of the connecting element 120 is inserted through the notch 228 of the actuating lever 118 and the connecting pin 121 is seated within notch 262 of the connecting element 120, thus providing for a sliding movement of the connecting element 120 relative handle element 102 along longitudinal axis, such as for example axis 240. Biasing spring 122 is seated in 168 of handle element 102 and supported against connecting element 120.

In some embodiments, hollow shaft element 110 remains partially inserted into handle element 102, namely the proximal end 112 of the hollow shaft element 110 is inserted into semi-circular groove 164 of handle element 102 and fixedly held therewithin by engagement of connecting pins 115 with notches 276 of hollow shaft 110 and recesses 166 of groove 164 of handle element 102.

In some embodiments, adaptor element 116 remains fixedly connected to hollow shaft 110 or integrally made therewith.

In some embodiments, needle retaining element 124 remains fixedly inserted within connecting element 120, such that proximal end 126 of needle retaining element 124 is inserted into longitudinal recess 248 of connecting element 120. In some embodiments, needle retaining element adaptor 130 remains fixedly coupled to needle retaining element 124. Needle element 140 remains in turn connected to needle retaining element adaptor 130 by means of engagement with connecting pins 141. Optionally, the connecting pins 141 are slidable within longitudinal apertures 296 of adaptor element 116.

It is a particular feature of some embodiments of the present invention that the sliding movement of the connecting element 120 is transferred to needle retaining element 124, in turn to needle retaining element adaptor 130 and finally to needle element 140. Optionally, due to this transfer and to the fact that connecting pins 141 are slidable within longitudinal apertures 296 of adaptor element 116, relative axial movement is provided between needle element 140 and the distal end 292 of adaptor element 116.

In some embodiments, locking lever 142 remains hingedly connected to handle element 102 by means of connecting pin 143. In some embodiments, retaining element 146 remains hingedly connected to handle element 102 by means of connecting pin 147 and is enclosed within handle element 102 by means of locking lever 142. Leaf spring 148 remains fixedly inserted into notch 180 of handle element 102 and biases retaining element 146 to engage locking lever 142 with curved portion 194 and further engage downwardly facing wall surface 254 of connecting element 120 with curved portion 196 thereof.

It is a particular feature of some embodiments of the present invention that in a closed operative orientation of the suture capturing device 100 the locking lever 142 is pressed upwardly, thus pushing the retaining element 146 against the force of leaf spring 148 and causing the curved portion 194 to disengage the proximally facing shoulder 256 and instead engage downwardly facing wall surface 254 of the connecting portion 120.

The disengagement of curved portion 194 from the proximally facing shoulder 256, provides for release of the biasing spring 122 and thus causes movement of the connecting element 120 in a proximal direction and lifting upwards of the actuating lever 118. The needle element 140 is in turn displaced proximally towards distal end 292 of adaptor element 116 and thus providing U-shaped recess 312 of the needle element 140 for locking the surgical suture between the needle element 140 and the distal end 292 and prevent the surgical suture from disengagement therefrom.

In some embodiments, in this closed operative orientation, engagement is provided between the proximal edges of the needle element 140 and recesses 298 of adaptor element 116.

It is a further particular feature of some embodiments of the present invention that components holding the surgical suture are rigid, namely the needle element 140, the hollow shaft 110 and adaptor element 116 are also optionally rigid elements, which provide for a fully controlled operation of the suture capturing device 100.

Reference is now made to FIGS. 13-16, which are simplified assembled view illustrations showing the various steps in the method of operation of the suture capturing device 100 of FIG. 1, according to some embodiments.

In some embodiments, the arthroscopic procedure includes the following actions:

In some embodiments, the suture capturing device 100 is positioned at the surgical site; the suture capturing device 100 is inserted through the patient's soft tissue. Optionally, several sutures are captured; The surgical suture is captured using the suture capturing device 100; The actuating lever 118 is pushed upon in order to secure the surgical suture therein; The locking lever 142 is pushed upon in order to lock the surgical suture within the suture capturing device 100; The suture capturing device 100 is withdrawn from the soft tissue; The suture capturing device 100 is reopened; The surgical suture is removed from the suture capturing device 100.

It is seen in FIG. 13 that the suture capturing device 100 is in an open operative orientation for example as shown in FIG. 10. In this open operative orientation, the suture capturing device 100 is operative for catching a surgical suture through the u-shaped open recess 312 of needle element 140.

It is seen in FIG. 14 that the suture capturing device 100 is still in an open operative orientation for example as shown in FIG. 10. In this open operative orientation, it is seen that the surgical suture is already captured by the suture capturing device 100.

It is seen in FIG. 15 that the suture capturing device 100 is a partially closed operative orientation for example as shown in FIG. 11. In this open operative orientation, it is seen that the surgical suture is already captured by the suture capturing device 100. The surgical suture is securely held within the suture capturing device 100 and prevented from disengagement therefrom, however allows for movement of the surgical suture therewithin.

It is seen in FIG. 16 that the suture capturing device 100 is in a closed operative orientation for example as shown in FIG. 12. In this open operative orientation, it is seen that the surgical suture is fixedly locked within the suture capturing device 100, prevented from disengagement therefrom, and prevented from movement relative thereto.

Figure 17:
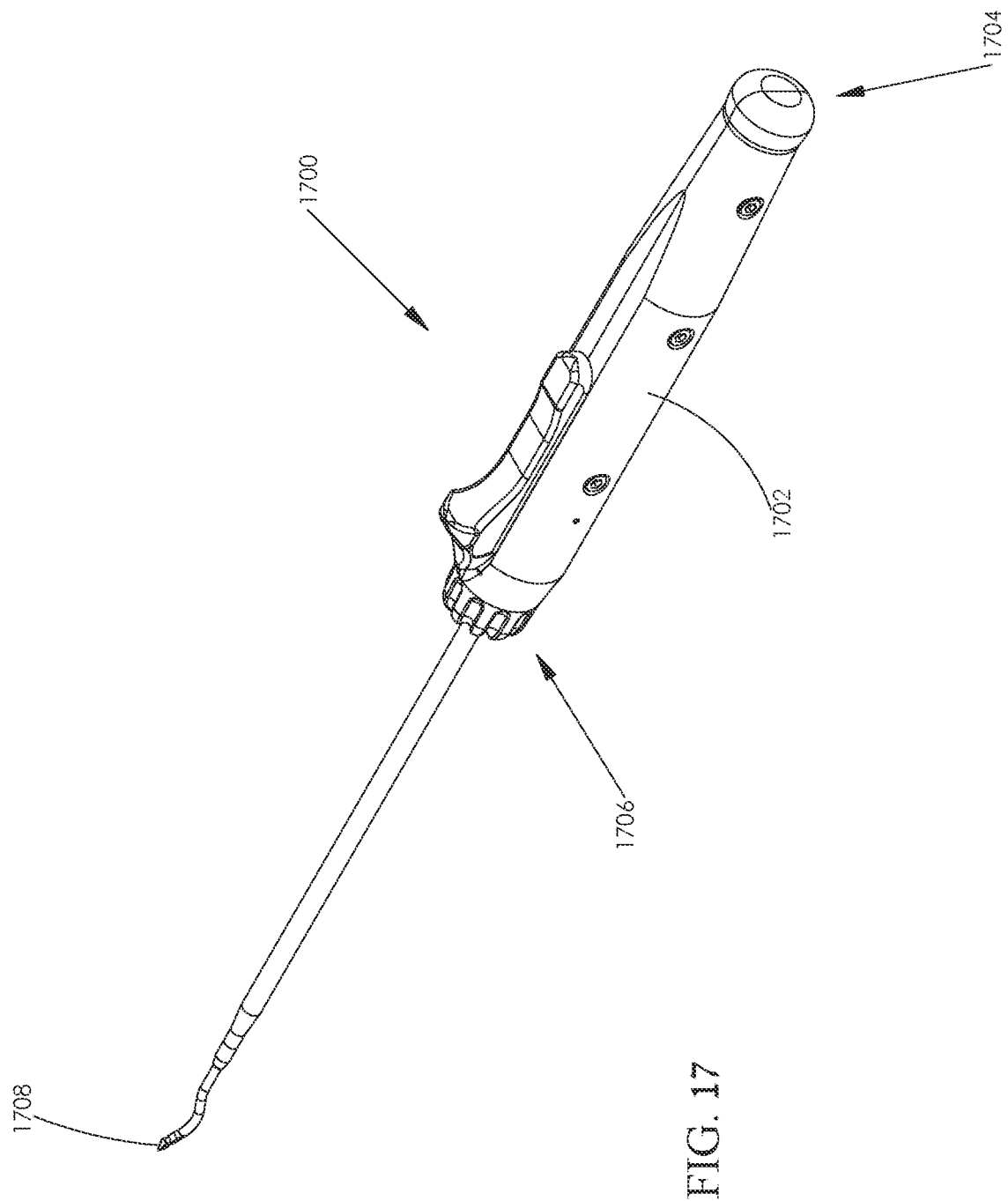
FIG. 17 is perspective view of a suture capturing device, in accordance with an exemplary embodiment of the invention.

FIG. 17 is perspective view of a suture capturing device 1700, in accordance with an exemplary embodiment of the invention. In an embodiment, the suture capturing device 1700 includes a handle element 1702, configured for use by a medical professional's hand. The handle element 1702 has a proximal end 1704 and a distal end 1706. The handle element 1702, located on a proximal end of the device, is located opposite a suture capturing needle element 1708, described in more detail below with respect to FIGS. 22 and 23A-23E. Generally speaking, the medical professional uses the distal end of the device 1700, the needle element 1708, to penetrate body tissue for inserting a suture into the body and/or for capturing and/or removing a suture from the body. Exemplary components/elements of the device 1700, modes of operation and methods of use are described herein.

Figure 18:
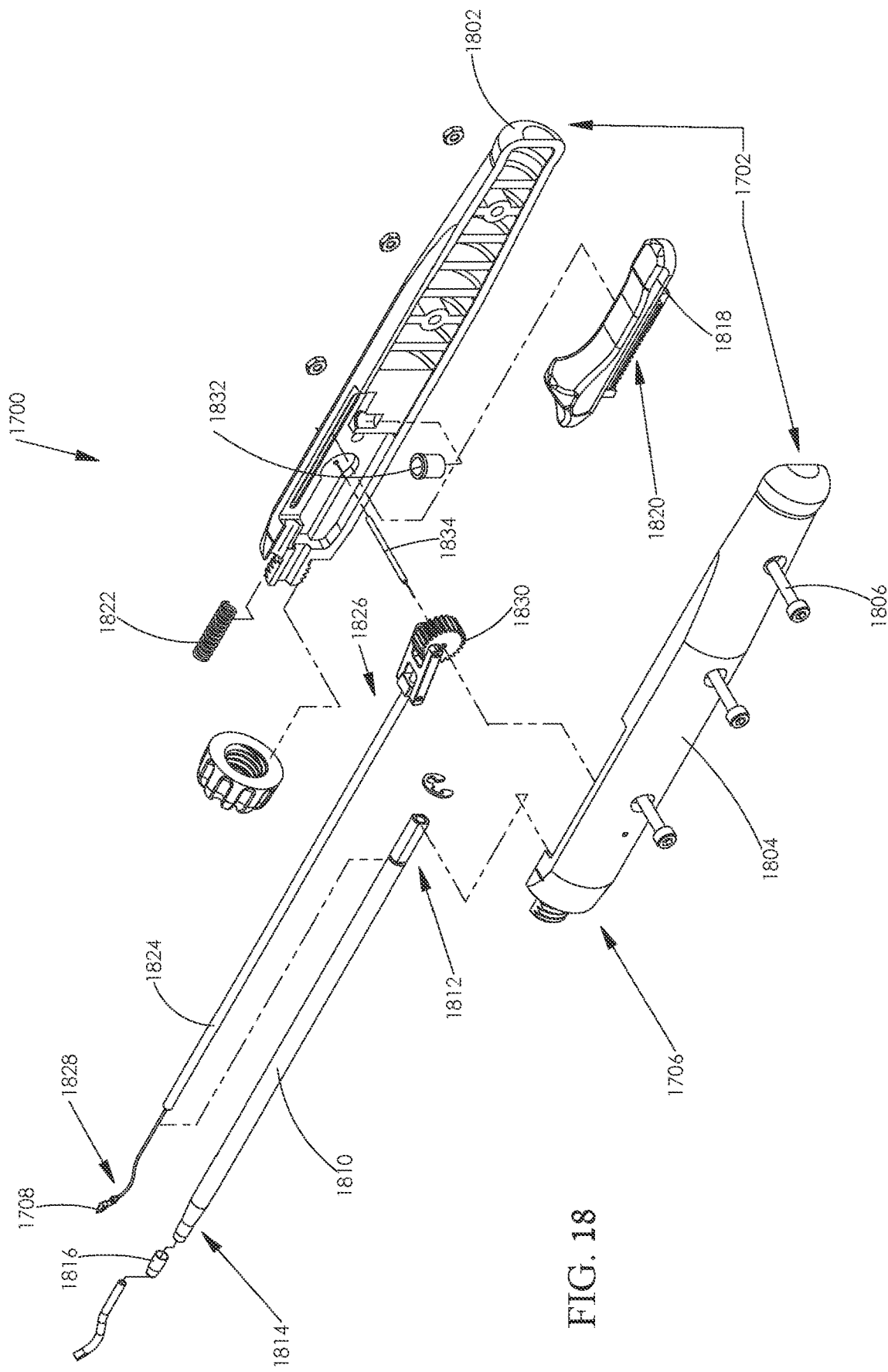
FIG. 18 is a simplified exploded view of the suture capturing device of FIG. 17, in accordance with an exemplary embodiment of the invention.

FIG. 18 is a simplified exploded view of the suture capturing device 1700 of FIG. 17, in accordance with an exemplary embodiment of the invention. Handle element 1702 includes two counterpart halves 1802, 1804 which are attached using at least one connector 1806, such as a screw, according to some embodiments. Alternatively and/or additionally, in some embodiments the two halves of the handle element 1702 can be connected using any other method such as welding, snap-fit or attachment by adhesive for example.

A hollow shaft 1810 has a proximal end 1812 and a distal end 1814. The proximal end 1812 of the hollow shaft 1810 is coupled with and, in some embodiments, at least partially inserted into the distal end 1706 of handle element 1702, optionally secured into the handle 1702 using connecting pins, screws, adhesive, compression/snap fit or the like. In some embodiments, additional hollow parts 1816 are used with shaft 1810 to provide a conduit for a needle retaining rod 1824, described in more detail below.

In some embodiments, an actuating slide 1818 is partially and slidably inserted between the two halves of handle element 1702 such that a lower portion of the actuating slide 1818 is retained within the body of the handle 1702, while a user operable portion remains outside of the body of the handle 1702. In some embodiments, the bottom of the actuating slide 1818 is provided with teeth 1820, designed to act as counterparts to a toothed wheel, described in more detail below.

In some embodiments, a needle retaining element 1824 extends within hollow shaft 1810 and has a proximal end 1826 and a distal end 1828. In some embodiments, the proximal end 1826 of the needle retaining element 1824 is hingedly coupled to toothed wheel 1830, where the toothed wheel 1830 is axially and rotatably attached to the halves 1802, 1804 by a pin 1834. The toothed wheel 1830 is provided with teeth which act as counterparts to the teeth 1820 of the actuating slide 1818, such that when the slide 1818 is moved, the toothed wheel 1830 rotates clockwise or counterclockwise depending on the direction of movement of the slide 1818. In some embodiments, the distal end 1828 of the needle retaining element 1824 is configured to be more flexible than the needle retaining element 1824 and/or the shaft 1810. The distal end 1828 is integrally formed with the needle retaining element 1824 or is coupled to it, in some embodiments.

In some embodiments, a biasing spring 1822 is provided. In some embodiments, the spring 1822 is inserted into the distal end 1706 of handle element 1702 until it abuts a distal end of the actuating slide 1818. The biasing spring 1822 is configured to bias the device 1700 in a closed operative orientation, described elsewhere herein, and shown in FIGS. 19A-19C.

Figure 19:
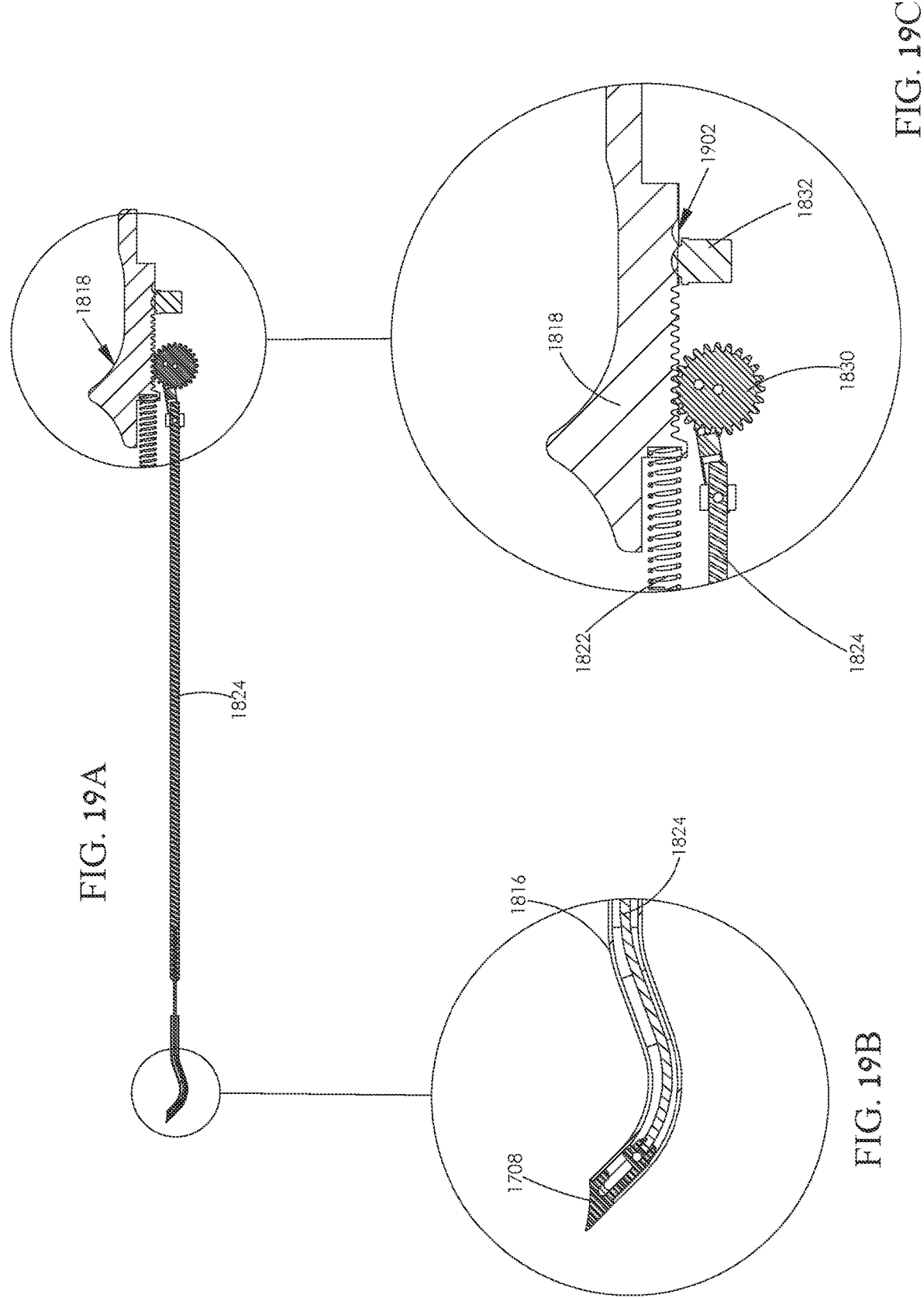
FIGS. 19A-19C are simplified side, cross-sectional views of the device of FIG. 17 showing the device in a closed operative orientation, in accordance with an exemplary embodiment of the invention.

A tab 1832 is provided to the device 1700 as a counterpart to a notch 1902, shown in more detail in FIG. 19C, in the actuating slide 1818. In an embodiment of the invention, the notch 1902 is deep enough and the tab 1832 fills the notch 1902 enough to prevent sliding of the actuating slide 1818 solely from force of the biasing spring 1822 (when the tab is in the notch).

FIGS. 19A-19C are simplified side, cross-sectional views showing the device 1700 in a closed operative orientation, in accordance with an exemplary embodiment of the invention. In an embodiment, "closed" means that the needle element 1708 is retracted into the shaft 1810, or at least a hollow part 1816 connected to the shaft 1810, such that the pointed distal tip of the needle element 1708 remains uncovered while suture catching structures (described in more detail with respect to FIGS. 22 and 23A-23E) of the needle element 1708 are covered. In an embodiment, in the closed orientation the actuating slide 1818 is positioned in a backwards (relative to handle 1702) or proximal configuration and where the biasing spring 1822 is un-compressed. The tab 1832 is located distally of the notch 1902, in some embodiments. It should be understood that the actuating slide 1818 is slidable distally and proximally (or from the perspective of this Figure, left and right, respectively) and the tab 1832 remains in a stable position during slide 1818 movement, held in place by the two halves 1802, 1804. FIGS. 19B and 19C are enlarged views of particular areas of device 1700.

Figure 20:
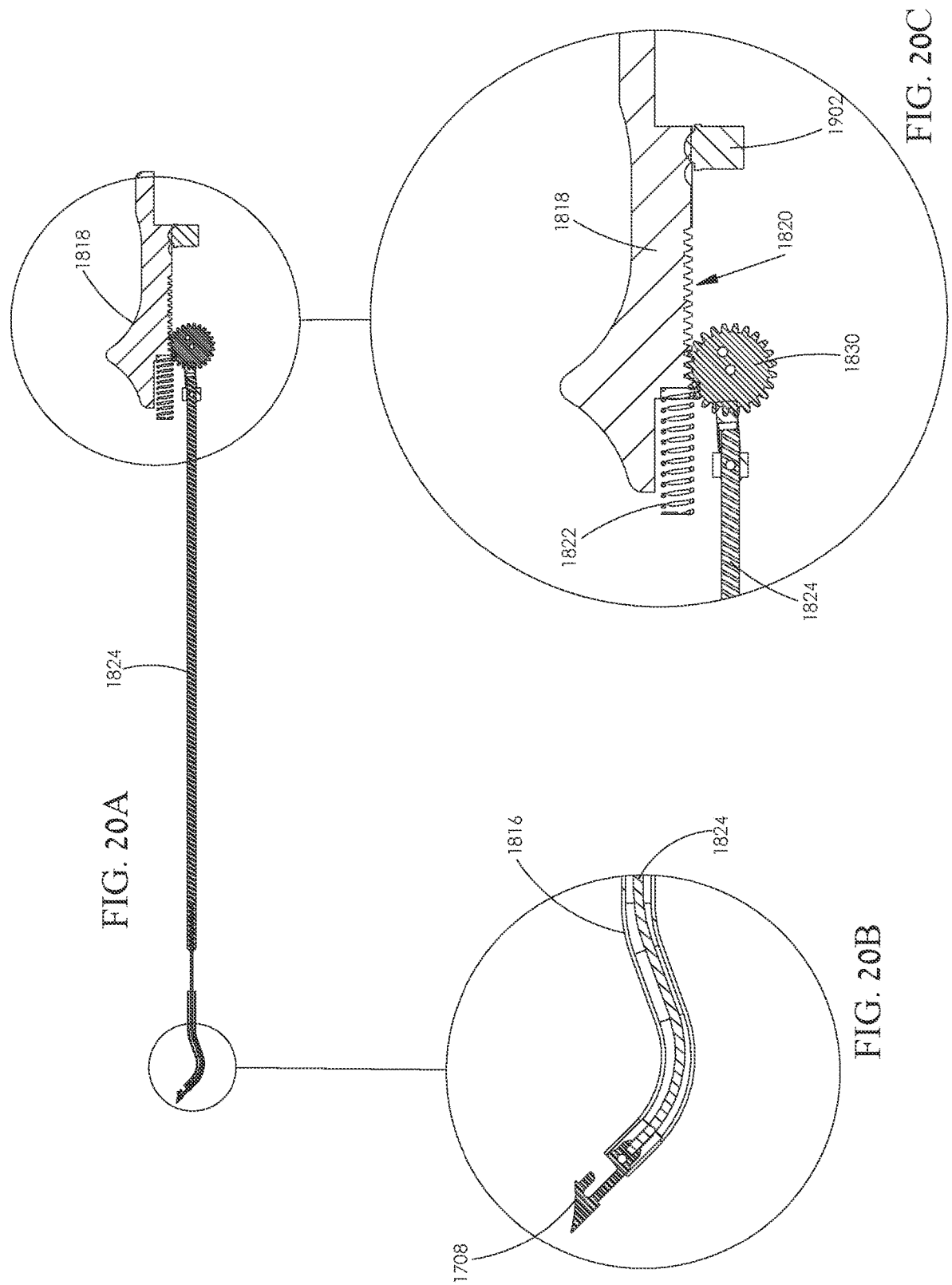
FIGS. 20A-20C are simplified side, cross-sectional views of the device of FIG. 17 showing the device in an open operative orientation, in accordance with an exemplary embodiment of the invention.

FIGS. 20A-20C are simplified side, cross-sectional views of the device of FIG. 17 showing the device in an open operative orientation, in accordance with an exemplary embodiment of the invention. In an embodiment, "open" means that the needle element 1708 is extended out of the shaft 1810, or at least a hollow part 1816 connected to the shaft 1810, such that the pointed distal tip of the needle element 1708 and suture catching structures of the needle element 1708 are fully uncovered. In an embodiment, in the open orientation the actuating slide 1818 is positioned in a forwards or distal configuration and where the biasing spring 1822 is compressed, having been pushed by the forward movement of the slide 1818. The tab 1832 is shown being located proximally of the notch 1902, the slide 1818 having moved to the left in this Figure or distally (relative to the handle 1702) and over the tab 1832 past the notch 1902. Movement of the slide 1818 distally translates to movement of teeth 1820 relative to the toothed wheel 1830, effectuating rotation of the toothed wheel 1830 in a counterclockwise fashion and the extension of the needle element 1708 out of the shaft 1810. FIGS. 20B and 20C are enlarged views of particular areas of device 1700.

Figure 21:
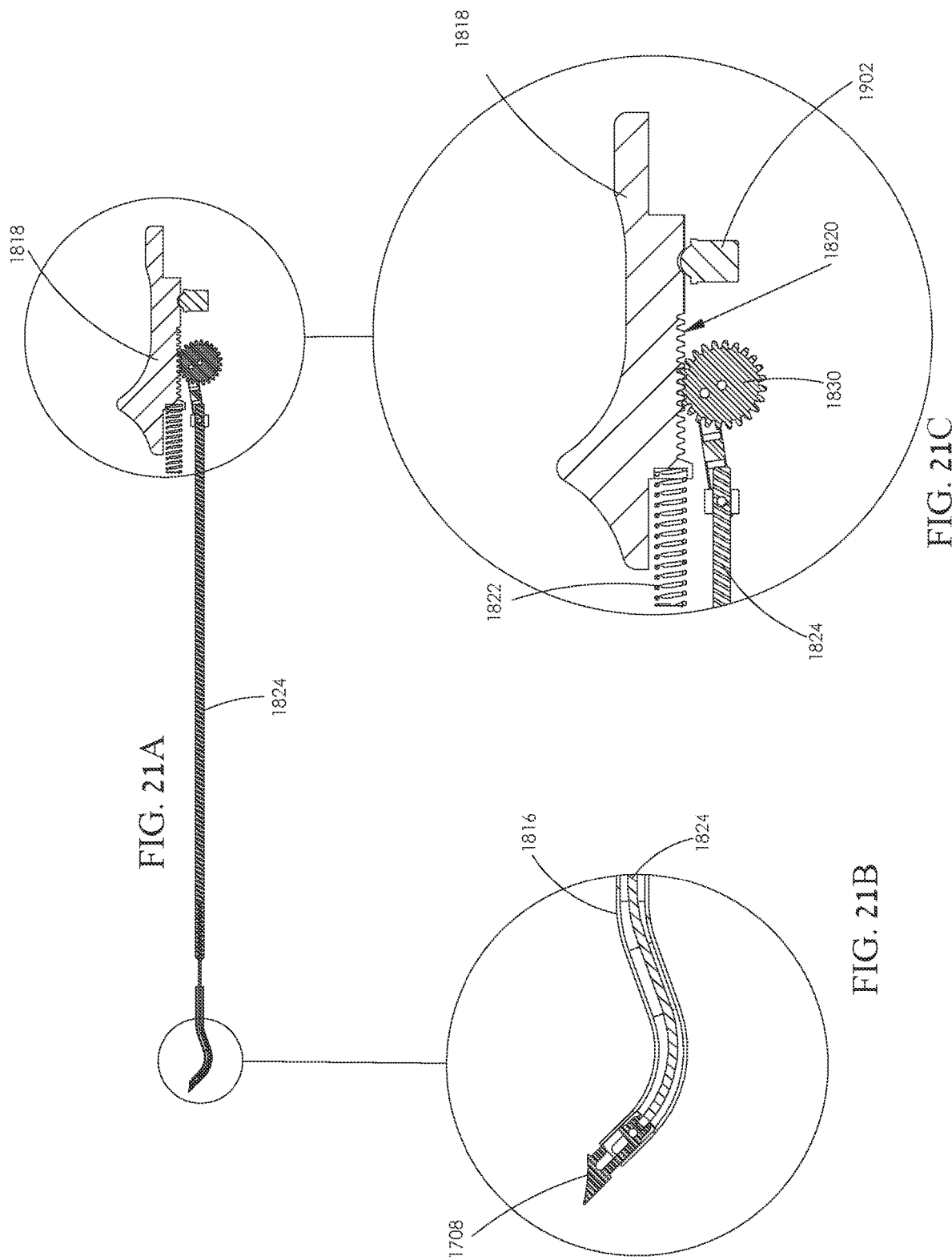
FIGS. 21A-21C are simplified side, cross-sectional views of the device of FIG. 17 showing the device in a partially closed operative orientation, in accordance with an exemplary embodiment of the invention.

FIGS. 21A-21C are simplified side, cross-sectional views of the device of FIG. 17 showing the device in a partially closed operative orientation, in accordance with an exemplary embodiment of the invention. In an embodiment, "partially closed" means that the needle element 1708 is extended out of the shaft 1810, or at least a hollow part 1816 connected to the shaft 1810, such that although the pointed distal tip of the needle element 1708 is fully uncovered, the suture catching structures of the needle element 1708 are covered sufficiently to prevent them from catching or hooking something. In an embodiment, in the partially closed orientation the actuating slide 1818 is positioned in a middle configuration relatively, between the open and closed orientations, and where the biasing spring 1822 is at least slightly less compressed than in the open orientation. The tab 1832 is shown being located within the notch 1902, the notch 1902 being placed on the slide 1818 at a pre-determined position which correlates to the suture catching structures of the needle element 1708 being covered and prevented from catching or hooking something. In an embodiment, the notch 1902 is at least partially provided to give a user of the device 1700 a tactile sensation of the location of the pre-determined partially closed orientation. In an embodiment, the slide 1818 is shown having moved to the right or proximally in this view (with respect to the immediate previous position shown in FIGS. 20A-20C). Movement of the slide 1818 proximally translates to movement of teeth 1820 relative to the toothed wheel 1830, effectuating rotation of the toothed wheel 1830 in a clockwise fashion and the partial retraction of the needle element 1708 into the shaft 1810. FIGS. 21B and 21C are enlarged views of particular areas of device 1700.

Figure 22:
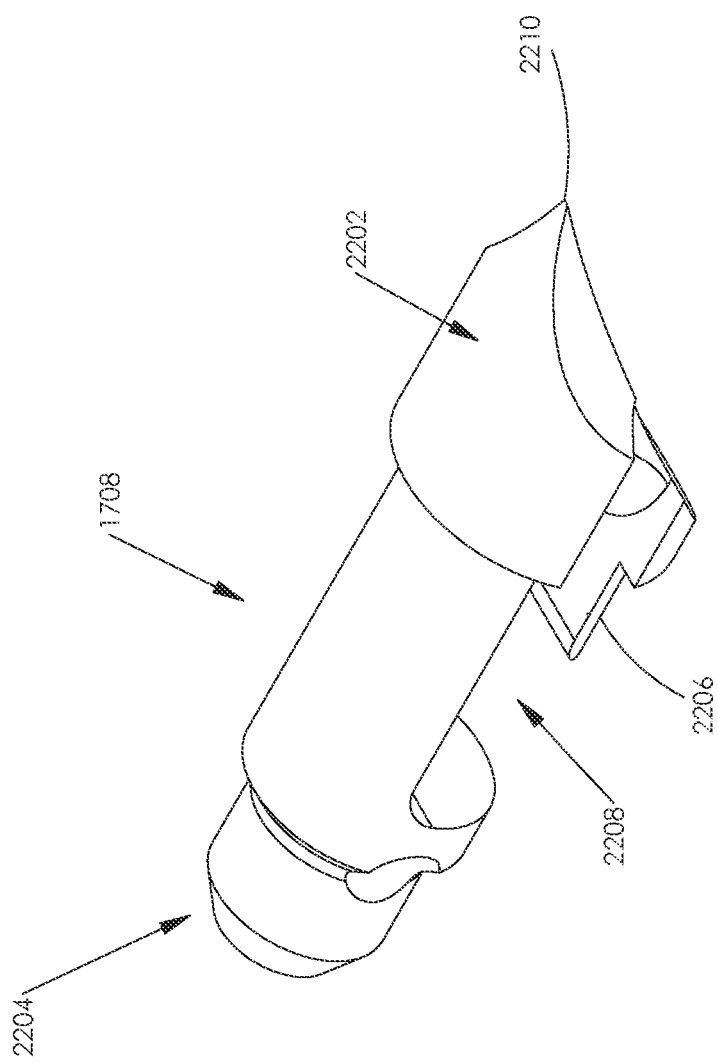
FIG. 22 is a perspective view of a suture capturing needle element of the device of FIG. 17, in accordance with an exemplary embodiment of the invention.

FIG. 22 is a perspective view of a suture capturing needle element 1708 of the device 1700, in accordance with an exemplary embodiment of the invention. In an embodiment, the needle element 1708 has a distal end 2202 and a proximal end 2204, where the distal end 2202 is configured with a sharp tip 2210 to penetrate body tissue and the proximal end 2204 is configured to mate with a distal end of the needle retaining element 1824. In some embodiments, the needle element 1708 has a hook 2206 for capturing or hooking something, for example a suture. A space 2208 is provided to the needle element 1708 to assist with catching or hooking using the hook 2206. In an embodiment, the space 2208 extends "under" the hook 2206, between the hook 2206 and the main body of the needle element 1708.

FIGS. 23A-23E show top, front, side, back and bottom views, respectively, of the suture capturing needle element 1708, in accordance with an exemplary embodiment of the invention. In some embodiments, needle element 1708 is generally formed as an integral element made of a rigid material, such as titanium or any other biocompatible material, and is generally arranged along and/or around a longitudinal axis 2304.

Figure 23D:
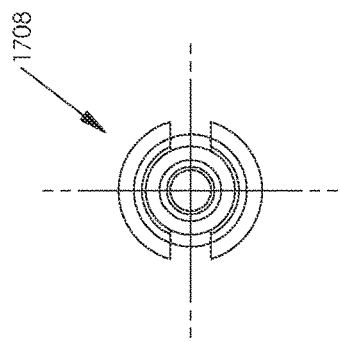
FIGS. 23A-23E show top, front, side, back and bottom views, respectively, of the suture capturing needle element of FIG. 22, in accordance with an exemplary embodiment of the invention.
Figure 23A:
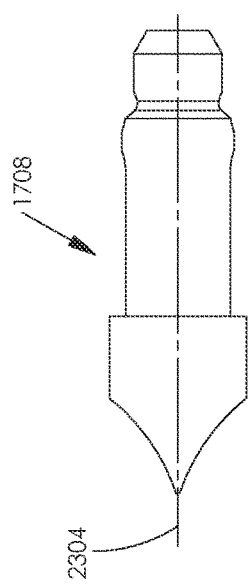
Figure 23C:
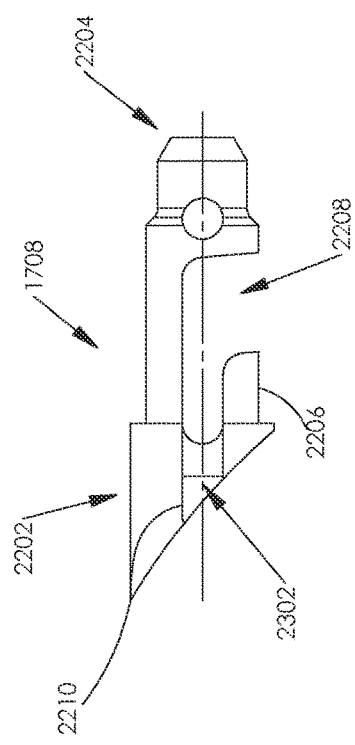
Figure 23E:
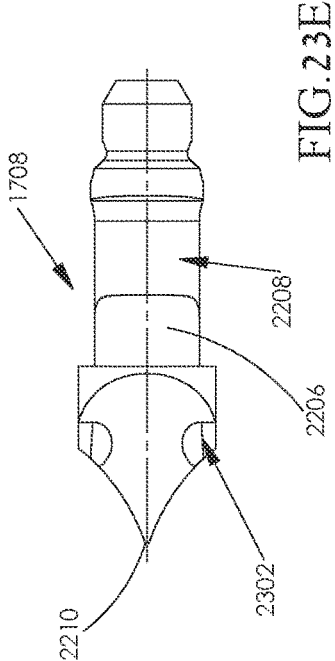
Figure 23B:
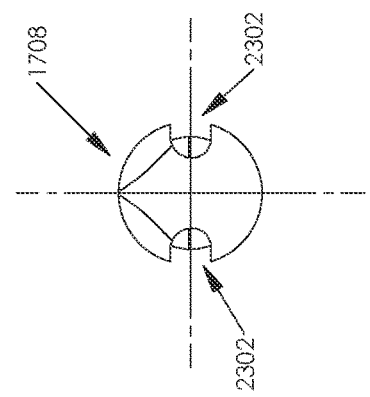

FIGS. 23B, 23C and 23E show in more detail recesses 2302 configured to accommodate a surgical suture therein, particularly when the suture has been caught by the hook 2206. In an embodiment of the invention, the recesses 2302 form a U-shape with the connecting portion of the U traversing the space 2208 under the hook 2206. FIGS. 23A-23E show the sharp tip 2210 and its tissue penetrating configuration in more detail. In some embodiments of the invention, a leading edge of the sharp tip 2210 is curved, optionally to enhance penetrative ability while retaining the ability to spread penetrated tissue after the most distal part of the tip 2210 has already passed therethrough.

Figure 34:
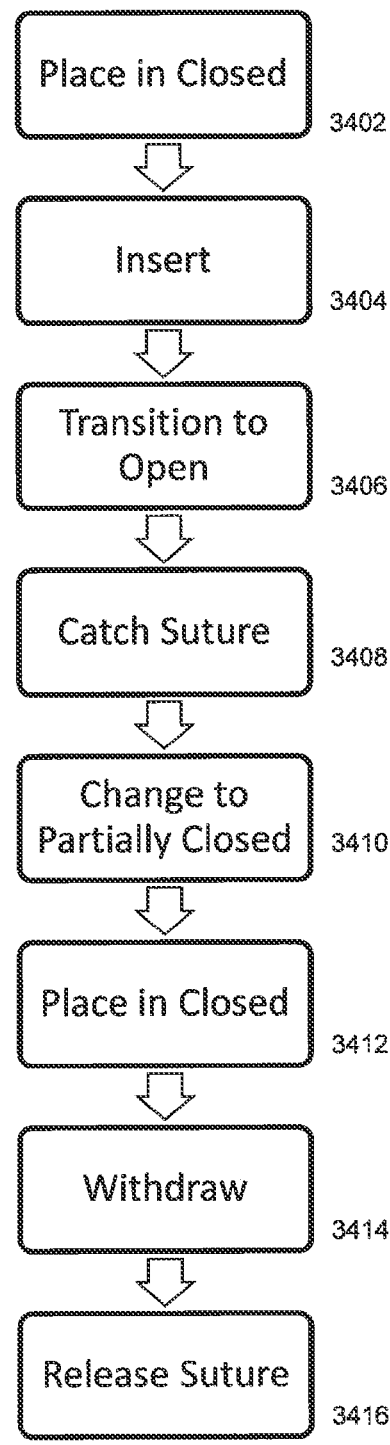
FIG. 34 is a flowchart of a method of using the device of FIG. 17 to withdraw a suture from the body, in accordance with an exemplary embodiment of the invention; and, FIG. 35 is a flowchart of a method of using the device of FIG. 17 to insert a suture into the body, in accordance with an exemplary embodiment of the invention.

FIGS. 24A-28C show sequentially the device 1700 configurations and procedure for retrieving a suture from inside body tissue, in some embodiments of the invention. For efficiency, FIGS. 24A-28C are described in conjunction with the flowchart of the method shown in FIG. 34.

FIGS. 24A-24C show the device 1700 placed (3402) in closed orientation for insertion (3404) into body tissue 2400 in order to catch (3408) a suture 2402 from the body tissue 2400, in accordance with an exemplary embodiment of the invention. It can be seen that in the closed orientation, the slide 1818 is positioned proximally (to the right, from this perspective) on the device 1700 of a mid-point indicator 2404, the location of which corresponds to the partially closed orientation when the tab 1832 is within the notch 1902.

FIGS. 25A-25C show the device 1700 inserted (3404) into the body 2400 and transitioned (3406) to an open orientation for catching (3408) the suture 2402, in accordance with an exemplary embodiment of the invention. In the open orientation, the slide 1818 is moved distally (to the left, from this perspective) and past the indicator 2404 to extend the needle element 1708 out of the device 1700 in anticipation of hooking/catching (3408) the suture 2402 on the hook 2206.

FIGS. 26A-26C show the device 1700 inserted (3404) into the body 2400 and changed (3410) to a partially closed orientation having a suture 2402 captured (3408) by hook 2206, in accordance with an exemplary embodiment of the invention. In the partially closed orientation, the device 1700 is configured so that when the slide 1818 is aligned with the indicator 2404, the tab 1832 is positioned within the notch 1902. In an embodiment, when the device 1700 is in partially closed orientation the hook 2206 is drawn to abut the end of the shaft 1810 or part 1816 such that a minimal or no gap exists between the hook 2206 and the shaft 1810 or part 1816 (thereby trapping the suture 2402 within the tip 1708).

As described elsewhere herein, movement of the slide 1818 distally compresses the biasing spring 1822 such that release by the user of exerted distal pressure on the slide 1818 results in at least a partial return of the slide 1818 in a proximal direction. Optionally, release of the exerted pressure on the slide 1818 returns the device 1700 to the partially closed orientation. Optionally, release of the exerted pressure on the slide 1818 returns the device 1700 to the closed orientation. It should be understood that, in some embodiments of the invention, the suture is slidable through the space 2208 but is trapped within the space by the hook 2206 and the shaft 1810 or part 1816. In some embodiments of the invention, when the device 1700 is in the closed orientation the suture 2402 is pinned against the tip 1708 by the shaft 1810 or part 1816 and is not slidable.

FIGS. 27A-27C show the device 1700 having been placed (3412) in a closed orientation for withdrawal (3414) from the body 2400 and having been actually withdrawn (3414) from the body 2400, in accordance with an exemplary embodiment of the invention.

FIGS. 28A-28C show the device 1700 in an open operative orientation for releasing (3416) the suture 2402 outside the body 2400 where the suture 2402 is unhooked from the hook 2206, in accordance with an exemplary embodiment of the invention. In some embodiments, only a portion of the suture 2402 is retrieved from the body tissue 2400 and the rest remains inside the body 2400.

Figure 35:
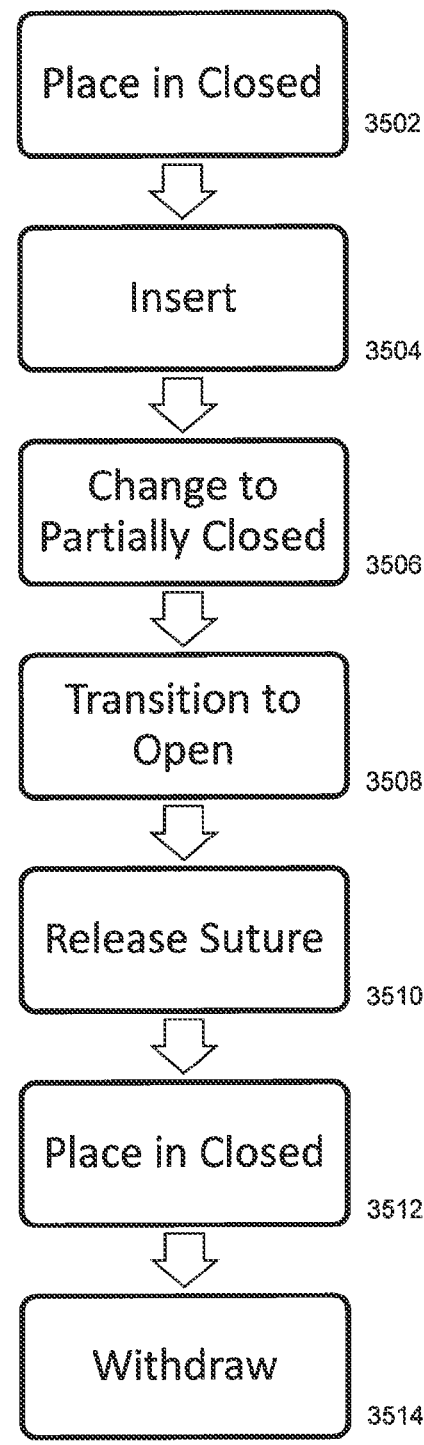

FIGS. 29A-33C show sequentially the device 1700 configurations and procedure for inserting a suture into body tissue, in some embodiments of the invention. For efficiency, FIGS. 29A-33C are described in conjunction with the flowchart of the method shown in FIG. 35.

FIGS. 29A-29C show the device 1700 placed (3502) in a closed orientation for insertion (3504) of a suture 2402 into a body 2400, in accordance with an exemplary embodiment of the invention. As described elsewhere herein, the slide 1818 is proximally located and the needle tip 1708, along with the suture 2402 to be implanted, are in a retracted configuration in the device 1700.

Figure 30C:
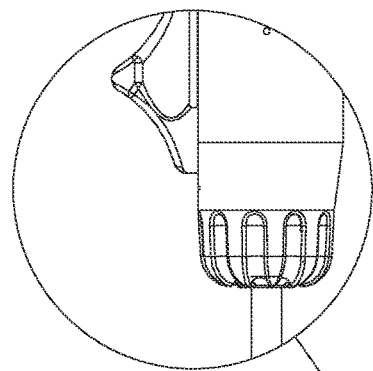
FIGS. 30A-30C show a device of FIG. 17 in a closed orientation just after insertion of a suture into a body, in accordance with an exemplary embodiment of the invention.
Figure 30A:
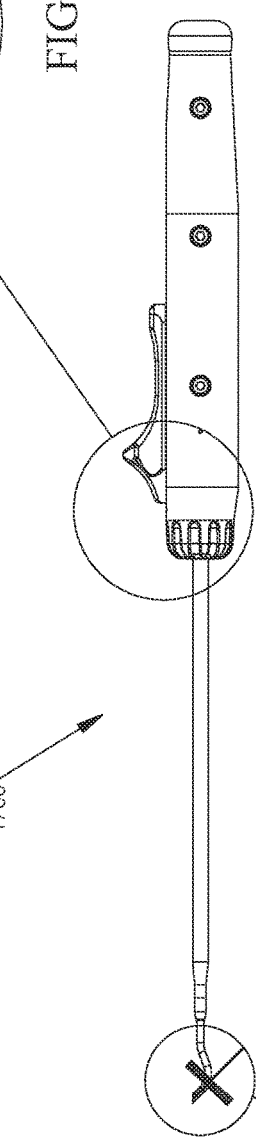
Figure 30B:
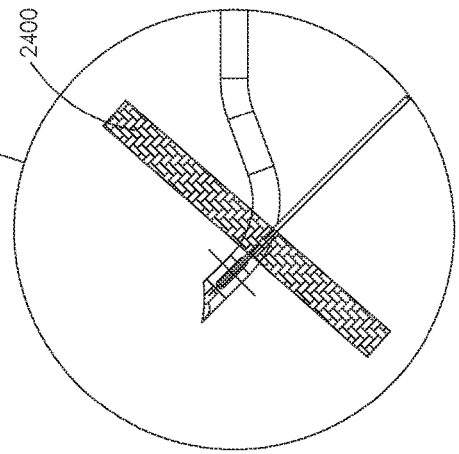

FIGS. 30A-30C show the device 1700 inserted (3504) in a closed orientation into the body 2400, in accordance with an exemplary embodiment of the invention.

FIGS. 31A-31C show the device 1700 changed (3506) to a partially closed orientation in preparation for release (3510) of the suture 2402, in accordance with an exemplary embodiment of the invention. In an embodiment, after changing (3506) the suture 2402 starts to be movable within the tip 1708 where in the partially closed orientation the suture is slidable within the space 2208 but is still trapped within the space 2208 by the hook 2206 and at least one of the hollow shaft 1810 or part 1816.

FIGS. 32A-32C show the device 1700 fully transitioned (3508) into an open orientation for releasing (3510) the suture 2402, in accordance with an exemplary embodiment of the invention. In an embodiment, the suture 2402 begins fully releasing out of the hook 2206 of the tip 1708 once the device is transitioned (3508).

FIGS. 33A-33C show the device 1700 withdrawn (3514) from the body 2400 after being placed (3512) in a closed orientation and after releasing (3510) the suture 2402 in the body 2400, in accordance with an exemplary embodiment of the invention. In some embodiments, only a portion of the suture 2402 is implanted into the body tissue 2400 and the rest remains outside the body 2400. Optionally, all of the suture 2402 is inserted into the body 2400 by the device 1700.

It will be appreciated by persons skilled in the art that the present invention is not limited by what has been particularly shown and described hereinabove. Rather the scope of the present invention includes both combinations and sub-combinations of various features described hereinabove as well as variations and modifications thereof which are not in the prior art.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A suture capturing device configured to attain multiple preset orientations, comprising:
    a handle; a hollow shaft coupled to said handle, said shaft having a distal end, said shaft distal end having a distal face;
    a recess defined in said distal face, wherein said recess defines a distally facing recessed surface;
    a rigid needle element having a distal tip and configured with a hook for catching a suture and where the needle element is operatively coupled to the hollow shaft opposite the handle and configured to be slidable in a first direction to assume an open orientation where the hook is exposed relative to the hollow shaft and in a second direction to assume a closed orientation where the hook is not exposed relative to the hollow shaft, wherein, in the closed orientation, said tip extends distally relative to a distal end of said hollow shaft and a proximal facing portion of said needle element directly contacts said shaft distal face to prevent further sliding of said needle element in said second direction; and
    wherein, in the closed orientation, said proximal facing portion of said needle element is in direct contact with said distally facing recessed surface, and said direct contact with said distally facing recessed surface prevents said further sliding of said needle element in said second direction.

2. A device according to claim 1, further comprising a configuration for a partially closed orientation wherein said needle element is placed in an intermediate position between the open and closed orientations such that the hook is not exposed but the needle element is at least partially extended from the hollow shaft.

3. A device according to claim 2, further comprising an actuating slide on the handle and operatively connected to the needle element for sliding the needle element distally and proximally.

4. A device according to claim 3, further comprising a toothed wheel operatively connected to the needle element where rotation of the wheel effectuates proximal and distal sliding of the needle element.

5. A device according to claim 4, further comprising teeth on a bottom of the actuating slide configured as counterparts to the toothed wheel, such that movement of the actuating slide teeth cause movement of the toothed wheel.

6. A device according to claim 3, further comprising a tab located in the handle and configured as a counterpart to a notch on a bottom of the actuating slide.

7. A device according to claim 6, further comprising an indicator on the top of the handle where when the tab is located in the notch, the front of the actuating slide is positioned at the indicator.

8. A device according to claim 7, configured such that when the front of the actuating slide is positioned at the indicator, the device is in the partially closed orientation.

9. A device according to claim 3, further comprising a biasing spring in the handle configured to bias the actuating slide in the closed orientation.

10. A device according to claim 3, wherein a toothed wheel is coupled to the needle element via a needle retaining element that displaces the needle element axially relative to said hollow shaft.

11. A device according to claim 10, wherein a distal end of the needle retaining element is more flexible than other portions of the needle retaining element and/or the shaft.

12. A device according to claim 3, wherein the hollow shaft comprises a distal curved hollow conduit for a needle retaining rod.

13. A device according to claim 2, wherein in the partially closed configuration said needle element is extended out of at least said hollow shaft such that at least a pointed distal tip of said needle element is fully uncovered and said hook is covered to avoid catching or hooking onto non-suture elements.

14. A device according to claim 1, where said tip of the needle element is a sharp tip configured for piercing body tissue.

15. A device according to claim 1, where the hollow shaft is rigid.

16. A device according to claim 1, wherein said recess comprises a pair of recesses each defining a distally facing recessed surface sized and shaped to engage said proximal facing portion of said needle element.

17. A device according to claim 1, wherein said recess comprises a pair of recesses each defining distally facing recessed surfaces and wherein, in said closed orientation, force is applied by said hook at said shaft distal face, between said recesses.

18. A device according to claim 1, wherein, in said closed orientation, a suture recess is provided between said shaft distal end and a portion of said needle element distal to said shaft distal end, said suture recess sized for locking a suture between said shaft distal end and said portion of said needle element distal to said shaft distal end.

19. A device according to claim 1, wherein said proximal facing portion includes a proximally facing protrusion at a location on said needle element opposite said hook and wherein, in the closed orientation, said proximal facing protrusion of said needle element is in direct contact with said distally facing recessed surface, and said direct contact of said protrusion with said distally facing recessed surface prevents said further sliding of said needle element in said second direction.

20. A device according to claim 19, wherein said proximally facing protrusion prevents axial movement and rotational movement of said needle element relative to said shaft.

21. A device according to claim 1, wherein said proximal facing portion includes at least two proximally facing protrusions; wherein said recess comprises a pair of recesses each defining a distally facing recessed surface; and wherein, in the closed orientation, said proximal facing protrusions are in direct contact with said distally facing recessed surfaces of said pair of recesses, and said direct contact of said protrusions with said distally facing recessed surfaces of said pair of recesses prevents said further sliding of said needle element in said second direction.

* * * * *

UNITED STATES PATENT AND TRADEMARK OFFICE
CERTIFICATE OF CORRECTION

| | | |
|---|---|---|
| PATENT NO. | : 11,020,107 B2 | Page 1 of 1 |
| APPLICATION NO. | : 15/557144 | |
| DATED | : June 1, 2021 | |
| INVENTOR(S) | : Mirochinik et al. | |

It is certified that error appears in the above-identified patent and that said Letters Patent is hereby corrected as shown below:

On the Title Page

Item (71) Applicants, Line 3:
Delete the following: "Alex Levin, Kiryat Yam (IL)"

Signed and Sealed this
Twenty-eighth Day of December, 2021

Drew Hirshfeld
*Performing the Functions and Duties of the*
*Under Secretary of Commerce for Intellectual Property and*
*Director of the United States Patent and Trademark Office*